United States Patent
Barker

(10) Patent No.: US 8,425,534 B2
(45) Date of Patent: *Apr. 23, 2013

(54) CAM LOCK BURR HOLE PLUG FOR SECURING STIMULATION LEAD

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1055 days.

This patent is subject to a terminal disclaimer.

(21) Appl. No.: 12/179,521

(22) Filed: Jul. 24, 2008

(65) Prior Publication Data

US 2010/0023100 A1    Jan. 28, 2010

(51) Int. Cl.
  *A61B 19/00* (2006.01)
  *A61N 1/05* (2006.01)

(52) U.S. Cl.
  USPC ............. 606/129; 606/130; 607/45; 607/116

(58) Field of Classification Search ............ 607/50, 607/115, 145, 149, 150
  See application file for complete search history.

(56) References Cited

U.S. PATENT DOCUMENTS

| | | | |
|---|---|---|---|
| 2,521,301 A | 9/1950 | Morrison | |
| 2,873,822 A | 2/1959 | Sloan | |
| 3,758,827 A * | 9/1973 | Schroder et al. | 361/247 |
| 3,826,952 A * | 7/1974 | Iwasaki et al. | 361/247 |
| 3,829,737 A * | 8/1974 | Johnsson | 361/247 |
| 4,245,645 A | 1/1981 | Arseneault et al. | |
| 4,297,609 A * | 10/1981 | Hirao et al. | 310/339 |
| 4,315,180 A * | 2/1982 | Kondo et al. | 310/319 |
| 4,328,813 A | 5/1982 | Ray | |
| 4,467,800 A | 8/1984 | Zytkovicz | |
| 4,741,571 A | 5/1988 | Godette | |
| 4,826,487 A | 5/1989 | Winter | |
| 4,850,359 A | 7/1989 | Putz | |
| 4,931,056 A | 6/1990 | Ghajar et al. | |
| 4,998,938 A | 3/1991 | Ghajar et al. | |
| 5,235,990 A * | 8/1993 | Dempsey | 607/145 |
| 5,464,446 A | 11/1995 | Dreessen et al. | |
| 5,484,445 A | 1/1996 | Knuth | |
| 5,496,356 A * | 3/1996 | Hudz | 607/72 |

(Continued)

FOREIGN PATENT DOCUMENTS

| | | |
|---|---|---|
| WO | WO 00/13743 A1 | 3/2000 |
| WO | WO 03/026738 A1 | 4/2003 |

(Continued)

*Primary Examiner* — Carl H Layno
*Assistant Examiner* — Roland Dinga
(74) *Attorney, Agent, or Firm* — Vista IP Law Group LLP

(57) ABSTRACT

A burr hole plug comprises a plug base configured for being mounted around a cranial burr hole. The plug base includes an aperture through which an elongated medical device exiting the burr hole may pass. The burr hole plug further comprises a retainer configured for being mounted within the aperture of the plug base. The retainer includes a retainer support, a slot formed in the retainer support for receiving the medical device, and a clamping mechanism having a movable clamping element and a cam configured for being rotated relative to the retainer support to linearly translate the movable clamping element into the slot, thereby securing the medical device. The retainer further comprises another clamping mechanism having another movable clamping element and another cam configured for being rotated relative to the retainer support to linearly translate the other movable clamping element, thereby laterally securing the retainer within the plug base.

17 Claims, 27 Drawing Sheets

U.S. PATENT DOCUMENTS

| | | | |
|---|---|---|---|
| 5,503,164 | A | 4/1996 | Friedman |
| 5,549,620 | A | 8/1996 | Bremer |
| 5,707,373 | A | 1/1998 | Sevrain et al. |
| 5,800,504 | A * | 9/1998 | Bellifemine ................ 607/145 |
| 5,843,150 | A | 12/1998 | Dreessen et al. |
| 5,865,842 | A | 2/1999 | Knuth et al. |
| 5,927,277 | A | 7/1999 | Baudino et al. |
| 5,954,687 | A | 9/1999 | Baudino |
| 6,006,124 | A | 12/1999 | Fischell et al. |
| 6,016,449 | A | 1/2000 | Fischell et al. |
| 6,044,304 | A | 3/2000 | Baudino |
| 6,050,998 | A | 4/2000 | Fletcher |
| 6,126,663 | A | 10/2000 | Hair |
| 6,128,538 | A | 10/2000 | Fischell et al. |
| 6,134,474 | A | 10/2000 | Fischell et al. |
| 6,230,049 | B1 | 5/2001 | Fischell et al. |
| 6,321,104 | B1 | 11/2001 | Gielen et al. |
| 6,354,299 | B1 | 3/2002 | Fischell et al. |
| 6,427,086 | B1 | 7/2002 | Fischell et al. |
| 6,459,936 | B2 | 10/2002 | Fischell et al. |
| 6,466,822 | B1 | 10/2002 | Pless |
| 6,480,743 | B1 | 11/2002 | Kirkpatrick et al. |
| 6,482,182 | B1 | 11/2002 | Carroll et al. |
| 6,597,954 | B1 | 7/2003 | Fischell et al. |
| 6,609,020 | B2 | 8/2003 | Gill |
| 6,618,623 | B1 | 9/2003 | Pless et al. |
| 6,647,296 | B2 | 11/2003 | Fischell et al. |
| 6,690,974 | B2 | 2/2004 | Archer et al. |
| 6,845,267 | B2 | 1/2005 | Harrison et al. |
| 6,920,359 | B2 | 7/2005 | Meadows et al. |
| 6,944,501 | B1 | 9/2005 | Pless |
| 6,950,707 | B2 | 9/2005 | Whitehurst |
| 7,004,948 | B1 | 2/2006 | Pianca et al. |
| 7,033,326 | B1 | 4/2006 | Pianca et al. |
| 7,090,661 | B2 | 8/2006 | Morris et al. |
| 7,174,213 | B2 | 2/2007 | Pless |
| 7,177,701 | B1 | 2/2007 | Pianca |
| 7,204,840 | B2 | 4/2007 | Skakoon et al. |
| 7,343,205 | B1 | 3/2008 | Pianca et al. |
| 7,421,297 | B2 | 9/2008 | Giftakis et al. |
| 7,454,251 | B2 | 11/2008 | Rezai et al. |
| 7,766,922 | B1 * | 8/2010 | Daglow et al. ................ 606/129 |
| 2001/0051819 | A1 | 12/2001 | Fischell et al. |
| 2001/0056290 | A1 | 12/2001 | Fischell et al. |
| 2002/0002390 | A1 | 1/2002 | Fischell et al. |
| 2002/0052610 | A1 * | 5/2002 | Skakoon et al. ................ 606/129 |
| 2002/0072770 | A1 | 6/2002 | Pless |
| 2002/0077670 | A1 | 6/2002 | Archer et al. |
| 2002/0099412 | A1 | 7/2002 | Fischell et al. |
| 2002/0169485 | A1 | 11/2002 | Pless et al. |
| 2003/0088274 | A1 | 5/2003 | Gliner et al. |
| 2004/0034367 | A1 | 2/2004 | Malinowski |
| 2004/0153129 | A1 | 8/2004 | Pless et al. |
| 2005/0015128 | A1 | 1/2005 | Rezai et al. |
| 2005/0075679 | A1 | 4/2005 | Gliner et al. |
| 2005/0075680 | A1 | 4/2005 | Lowry et al. |
| 2005/0182420 | A1 | 8/2005 | Schulte et al. |
| 2005/0182421 | A1 | 8/2005 | Schulte et al. |
| 2005/0182422 | A1 | 8/2005 | Schulte et al. |
| 2005/0182423 | A1 | 8/2005 | Schulte et al. |
| 2005/0182424 | A1 | 8/2005 | Schulte et al. |
| 2005/0182425 | A1 | 8/2005 | Schulte et al. |
| 2005/0182464 | A1 | 8/2005 | Schulte et al. |
| 2005/0222641 | A1 | 10/2005 | Pless |
| 2006/0212093 | A1 | 9/2006 | Pless et al. |
| 2006/0224216 | A1 | 10/2006 | Pless et al. |
| 2006/0229686 | A1 | 10/2006 | Giftakis et al. |
| 2007/0106143 | A1 | 5/2007 | Flaherty |
| 2007/0225773 | A1 | 9/2007 | Shen et al. |
| 2007/0233158 | A1 | 10/2007 | Rodriguez |
| 2008/0100061 | A1 | 5/2008 | Sage et al. |
| 2008/0172068 | A1 | 7/2008 | Adams et al. |
| 2008/0275466 | A1 | 11/2008 | Skakoon |
| 2010/0023020 | A1 | 1/2010 | Barker |

FOREIGN PATENT DOCUMENTS

| | | |
|---|---|---|
| WO | WO 2004/105640 A2 | 12/2004 |
| WO | WO 2004/105640 A3 | 12/2004 |
| WO | WO 2005/079903 A2 | 9/2005 |
| WO | WO 2005/079903 A3 | 9/2005 |
| WO | WO 2008/054691 A2 | 5/2008 |
| WO | WO 2008/054691 A3 | 5/2008 |
| WO | WO 2008/054699 A2 | 5/2008 |
| WO | WO 2008/054699 A3 | 5/2008 |
| WO | WO 2008/107815 A1 | 9/2008 |
| WO | WO 2008/107822 A1 | 9/2008 |
| WO | WO 2008/134509 A1 | 11/2008 |

* cited by examiner

CAM LOCK BURR HOLE PLUG FOR SECURING STIMULATION LEAD

RELATED APPLICATION

This application is filed concurrently with U.S. patent application Ser. No. 12/179,525, entitled "Cam Lock Burr Hole Plug for Securing Retainer/Plug Base", the disclosure of which is expressly incorporated herein by reference.

FIELD OF THE INVENTION

The present inventions relate to apparatus for securing elongated medical devices, such as catheters or leads, within a cranial burr hole.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation via stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical disorder for the treatment of advanced Parkinson's Disease. There have been approximately 30,000 patients world-wide that have undergone DBS surgery. Consequently, there is a large population of patients who will benefit from advances in DBS treatment options.

During DBS procedures, at least one burr hole is meticulously cut through the patient's cranium as not to damage the brain tissue below, a large stereotactic targeting apparatus is mounted to the patient's cranium, and a cannula is scrupulously positioned towards the target site in the brain. A stimulation lead is then introduced through the cannula, through the burr hole, and into the parenchyma of the brain, such that one or more electrodes located on the lead are strategically placed at a target site in the brain of the patient. Typically, an imaging device, such as a magnetic resonant imager (MRI), will be used to visualize the lead relative to the target site. Once the lead is properly positioned, the portion of the lead exiting the burr hole is subcutaneously routed underneath the patient's scalp to an implantable pulse generator (IPG) implanted in the patient at a site remote from the burr hole (e.g., the patient's shoulder or chest region). Further details discussing the treatment of diseases using DBS are disclosed in U.S. Pat. Nos. 6,845,267, 6,845,267, and 6,950,707, which is expressly incorporated herein by reference.

Significantly, it is crucial that proper location and maintenance of the lead position be accomplished in order to continuously achieve efficacious therapy. This is especially so with DBS applications, in which cases, the target site (or sites) that is intended for electrical stimulation is about the size of a pea and is located deep within the patient's brain. Thus, lead displacements of less than a millimeter may have a deleterious effect on the patient's therapy. Therefore, it is important that the electrode(s) of the lead be accurately located at the target site and that such electrode(s) be securely maintained at the target site during and after implantation of the lead.

To address these issues, a cranial burr hole plug is installed within the burr hole during the implantation procedure to hold the stimulation lead in place, as well as to seal the burr hole. Typically, the burr hole plug is composed of a multitude of components, including a ring-shaped base and a retainer that are integrated together to form the burr hole plug. Optionally, a cap may be further integrated with the base and retainer.

In particular, before the stimulation lead is introduced through the burr hole, the ring-shaped plug base is centered about the burr hole using a special centering tool that is disposed through the plug base into the burr hole, and is then permanently mounted to the patient's cranium using conventional means, such as bone screws. The stimulation lead is then introduced through the plug base and into the parenchyma of the brain. Notably, any displacement of the portion of the lead exiting the burr hole will result in the translation of the electrodes positioned in the brain relative to the target site, thereby requiring the lead to be repositioned—a time consuming process.

Thus, once the lead is properly located at the tissue site, the retainer is installed within the plug base (typically in an interference arrangement, such as a snap-fit arrangement) to secure the lead, thereby preventing migration of the lead relative to the target site during subsequent manipulation of the lead and installation of the optional cap. In one exemplary embodiment, the retainer comprises a disk having a slot for receiving the lead and a clamping mechanism that can be rotated within the slot towards a mating surface on the disk to frictionally clamp the received lead therebetween. The clamping mechanism may have one or more locking mechanisms that can engage or disengage complementary locking mechanisms on the disk to prevent rotation of the clamping mechanism. The portion of the stimulation lead exiting the retainer can then be bent downward towards the plane of the disk into a recess formed in the plug base, and the optional cap can be installed onto the plug base over the retainer to permanently secure the lead within the recess, as well as to seal the burr hole. Alternatively, instead of a cap, a biocompatible glue or other suitable adhesive can be used to seal the burr hole.

It can thus be appreciated from the foregoing that the burr hole plug serves as the platform for the entire DBS system, and therefore, it is important for this component to be robust, well-designed, and easy to use. Importantly, the burr hole plug should be designed, such that lead migration is minimized during installation of the burr hole plug. While prior art burr hole plugs have proven to be useful in the DBS context, there are still improvements that can be made.

For example, due mostly to their flexible nature and ability to lock in only one position, the clamping mechanisms of prior art burr hole plugs are not designed to firmly retain stimulation leads. As such, the stimulation lead may still inadvertently move even when it is supposedly secured by the clamping mechanism. Also, because these clamping mechanisms have only one set position when clamping down on a stimulation lead, prior art burr hole plugs are designed to be used with stimulation leads having one size. That is, the dimension between the retaining surface of the clamping device and the mating surface of the disk when the clamping device is in the locked position is designed to be slightly less than the diameter of the lead. If the diameter of the actual lead used with the burr hole plug is smaller than this intended diameter, the retention force applied to the lead by the clamping mechanism will not be sufficient. In contrast, if the diameter of the actual lead used with the burr hole plug is greater than this intended diameter, too much force will need to be applied to the lead in order to place the clamping mechanism within the locking position, thereby potentially damaging the retainer.

As another example of a problem suffered from prior art burr hole plugs, the retainer may rotate within the plug base, potentially resulting in the inadvertent movement of the stimulation lead from the target site. Such rotation of the retainer may typically occur in response to the manipulation of the clamping mechanism, and in particular, a downward force applied to the clamping mechanism that causes partial disengagement between the retaining disk to which the clamping mechanism is mounted and the plug base, and a lateral force applied to the clamping mechanism that causes the disengaged disk to rotate within the plug base.

As yet another example, once the plug base is mounted to the patient's cranium via bone screws, it is difficult to adjust the position of the plug base when desired. Also, due to the relatively large size of the stereotactic targeting apparatus, there is often little working space available between the targeting apparatus and the burr hole to secure the stimulation and to anchor the plug base to the cranium of the patient.

There, thus, remains a need for a burr hole plug that includes an improved means for securing a stimulation lead, for affixing the retainer to the plug base of the burr hole plug, and to anchor the burr hole plug within the burr hole formed in the cranium of a patient.

SUMMARY OF THE INVENTION

In accordance with a first aspect of the present inventions, a cranial burr hole plug is provided. The burr hole plug comprises a plug base configured for being mounted around a cranial burr hole. The plug base includes an aperture (e.g., a circular aperture) through which an elongated medical device exiting the burr hole may pass. The greatest dimension of the aperture may be, e.g., in the range of 10 mm-20 mm. In one embodiment, the burr hole plug further comprises fasteners configured for anchoring the plug base to a cranium of a patient. In another embodiment, the plug base comprises an inner annular flange configured for being disposed inside the cranial burr hole and an outer annular flange configured for being disposed outside of the cranial burr hole.

The burr hole plug further comprises a retainer configured for being mounted within the aperture of the plug base. In one embodiment, the retainer is removably mounted within the plug base aperture, although in other embodiments, the retainer is formed with, or otherwise permanently mounted to, the plug base. In another embodiment, the retainer includes at least one inner annular ledge configured for supporting the retainer when mounted within the plug base aperture.

The retainer further includes a retainer support, a slot formed in the retainer support for receiving the medical device (e.g., an open slot configured for laterally receiving the medical device), and a clamping mechanism having a movable clamping element and a cam configured for being rotated relative to the retainer support to linearly translate the movable clamping element into the slot, thereby securing the medical device. While the present inventions should not be so limited in their broadest aspects, the use of a cam provides a mechanical advantage for securing the medical device and provides a variable clamping force that can secure differently sized medical devices. In one embodiment, the retainer support includes a housing that contains the clamping mechanism. In this case, the retainer may further comprise a lid configured for being mounted to the housing to enclose the clamping mechanism. The housing may have a sidewall and an opening within the sidewall through which the movable clamping element is configured for linearly translating into the slot.

The retainer support may have a fixed clamping element on one side of the slot opposite the movable clamping element, such that the movable clamping element is configured for clamping the medical lead against the fixed clamping element. In one embodiment, the clamping mechanism further comprises a shaft rotatably mounted to the retainer support, in which case, the cam may be fixably disposed to the shaft. The shaft and cam may be eccentrically disposed relative to each other, and the shaft may be configured for receiving a tool for rotating the shaft. In this manner, the stimulation lead can be easily secured even when the space is quite limited by the stereotactic targeting apparatus. In another embodiment, the movable clamping element comprises a clamping flange configured for engaging the medical device and a cam follower element with which the cam slidably engages. The cam follower element may, e.g., be a collar circumferentially surrounding the cam.

In an optional embodiment, the cam is configured for being rotated relative to the retainer support to linearly translate the movable clamping element out of the slot, thereby releasing the medical device. In another optional embodiment, the retainer comprises another clamping mechanism having another movable clamping element and another cam configured for being rotated relative to the retainer support to linearly translate the other movable clamping element, thereby laterally securing the retainer within the plug base or securing the plug base within the cranial burr hole.

In accordance with a second aspect of the present inventions, another cranial burr hole plug is provided. The burr hole plug comprises a plug base configured for being mounted within a cranial burr hole. The greatest dimension of the aperture may be, e.g., in the range of 10 mm-20 mm. The cranial burr hole further comprises a slot formed in the plug base for receiving the medical device (e.g., an open slot configured for laterally receiving the medical device). The burr hole plug further comprises a clamping mechanism having a movable clamping element and a cam configured for being rotated relative to the plug base to linearly translate the movable clamping element into the slot, thereby securing the medical device. In one embodiment, the burr hole plug further comprises a lid configured for being mounted to the plug base to enclose the clamping mechanism. The plug base may have a sidewall extending along the slot and an opening within the sidewall through which the movable clamping element is configured for linearly translating into the slot.

The plug base may have a fixed clamping element on one side of the slot opposite the movable clamping element, such that the movable clamping element is configured for clamping the medical lead against the fixed clamping element. In one embodiment, the clamping mechanism further comprises a shaft rotatably mounted to the plug base, in which case, the cam may be fixably disposed to the shaft. The details of the shaft, cam, and movable clamping element can be the same as those described above.

In an optional embodiment, the cam is configured for being rotated relative to the plug base to linearly translate the movable clamping element out of the slot, thereby releasing the medical device. In another optional embodiment, the plug base has an annular wall configured for being disposed within the cranial burr hole and an opening formed within the annular wall, in which case, the burr hole plug may further comprise another clamping mechanism having another movable clamping element and another cam configured for being rotated relative to the retainer support to linearly translate the other movable clamping element through the opening, thereby securing the plug base within the cranial burr hole.

In accordance with a third aspect of the present inventions, still another cranial burr hole plug is provided. The burr hole plug comprises a plug base configured for being mounted around a cranial burr hole. The plug base includes an aperture (e.g., a circular aperture) through which an elongated medical device exiting the burr hole may pass. The greatest dimension of the aperture may be, e.g., in the range of 10 mm-20 mm. In one embodiment, the burr hole plug further comprises fasteners configured for anchoring the plug base to a cranium of a patient. In another embodiment, the plug base comprises an inner annular flange configured for being disposed inside the cranial burr hole and an outer annular flange configured for being disposed outside of the cranial burr hole.

The burr hole plug further comprises a retainer configured for being mounted within the aperture of the plug base. In one embodiment, the retainer is removably mounted within the plug base aperture, although in other embodiments, the retainer is formed with, or otherwise permanently mounted to, the plug base. In another embodiment, the retainer includes at least one inner annular ledge configured for supporting the retainer when mounted within the plug base aperture.

The retainer further includes a retainer support, a slot formed in the retainer support for receiving the medical device (e.g., an open slot configured for laterally receiving the medical device), and a clamping mechanism having a movable clamping element and a cam configured for being rotated relative to the retainer support to linearly translate the movable clamping element towards the plug base, thereby laterally securing the retainer within the plug base. While the present inventions should not be so limited in their broadest aspects, the use of a cam provides a convenient, efficient, and robust means for securing the retainer to the plug base. In one embodiment, the retainer support includes a housing that contains the clamping mechanism. In this case, the retainer may further comprise a lid configured for being mounted to the housing to enclose the clamping mechanism. The housing may have a sidewall and an opening within the sidewall through which the movable clamping element is configured for linearly translating towards the plug base. In another embodiment, the plug base comprises an inner annular flange configured for engaging the movable clamping element when linearly translated through the opening within the sidewall, thereby axially securing the retainer within the plug base.

In one embodiment, the clamping mechanism further comprises a shaft rotatably mounted to the retainer support, in which case, the cam may be fixably disposed to the shaft. The shaft and cam may be eccentrically disposed relative to each other, and the shaft may be configured for receiving a tool for rotating the shaft. In this manner, the retainer can be easily secured to the plug base even when the space is quite limited by the stereotactic targeting apparatus. In another embodiment, the movable clamping element comprises a clamping flange configured for engaging the plug base and a cam follower element with which the cam slidably engages. The cam follower element may, e.g., be a collar circumferentially surrounding the cam.

In an optional embodiment, the cam is configured for being rotated relative to the retainer support to linearly translate the movable clamping element away from the plug base, thereby releasing the retainer from the plug base. In another optional embodiment, the retainer comprises another clamping mechanism having another movable clamping element and another cam configured for being rotated relative to the retainer support to linearly translate the other movable clamping element, thereby laterally securing the medical device.

In accordance with a fourth aspect of the present inventions, yet another cranial burr hole plug is provided. The burr hole plug comprises a plug base having an annular sidewall configured for being mounted within a cranial burr hole and an opening formed through the annular sidewall. The greatest dimension of the aperture may be, e.g., in the range of 10 mm-20 mm. The cranial burr hole further comprises a slot formed in the plug base for receiving the medical device (e.g., an open slot configured for laterally receiving the medical device). The burr hole plug further comprises a clamping mechanism having a movable clamping element and a cam configured for being rotated relative to the plug base to linearly translate the movable clamping element through the opening in the annular sidewall, thereby securing the plug base to the cranial burr hole. While the present inventions should not be so limited in their broadest aspects, the use of a cam provides a means for reversibly anchoring the plug base within a burr hole. In one embodiment, the burr hole plug further comprises a lid configured for being mounted to the plug base to enclose the clamping mechanism. In one embodiment, the clamping mechanism further comprises a shaft rotatably mounted to the plug base, in which case, the cam may be fixably disposed to the shaft. The details of the shaft, cam, and movable clamping element can be the same as those described above.

In an optional embodiment, the cam is configured for being rotated relative to the plug base to linearly translate the movable clamping element inward through the opening in the sidewall, thereby releasing the plug base from the cranial burr hole. In another optional embodiment, the retainer comprises another clamping mechanism having another movable clamping element and another cam configured for being rotated relative to the plug base to linearly translate the other movable clamping element, thereby securing the medical device. In this case, the plug base may have a sidewall extending along the slot and an opening within the sidewall through which the other movable clamping element is configured for linearly translating into the slot.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
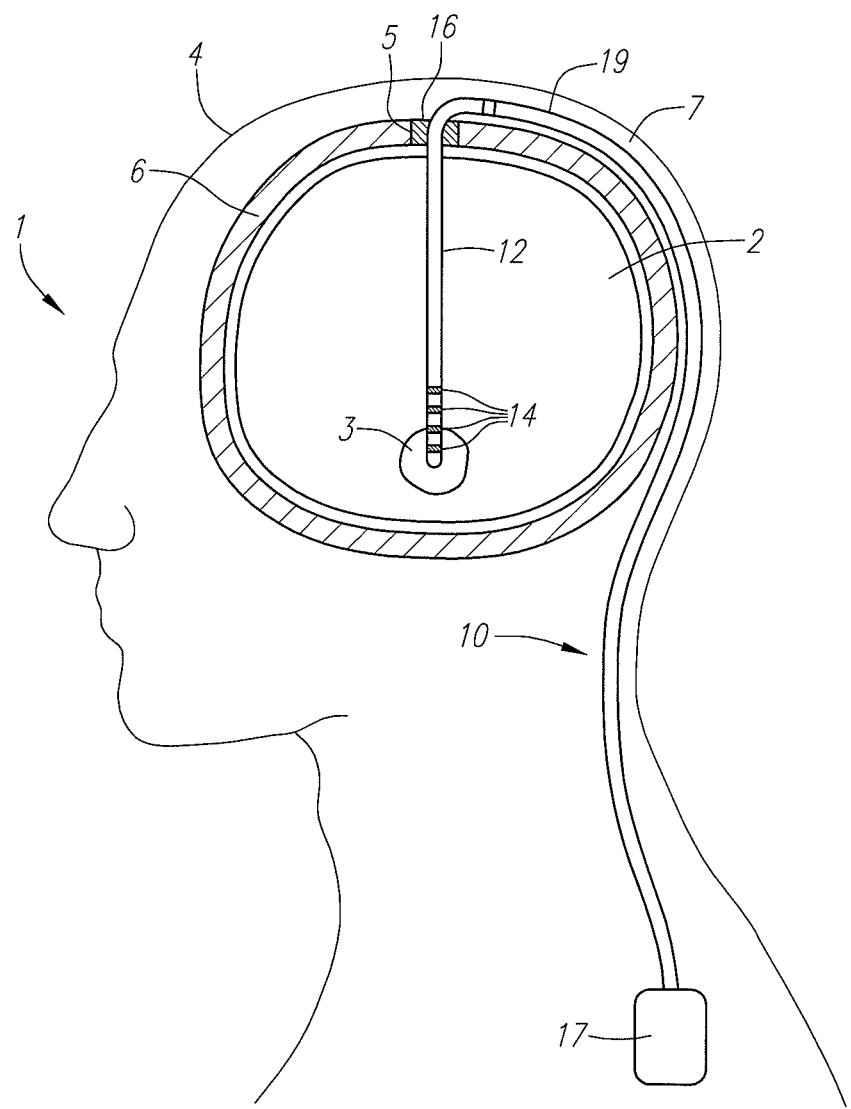
FIG. 1 is a plan view of a Deep Brain Stimulation (DBS) system implanted within a patient.
Figure 2:
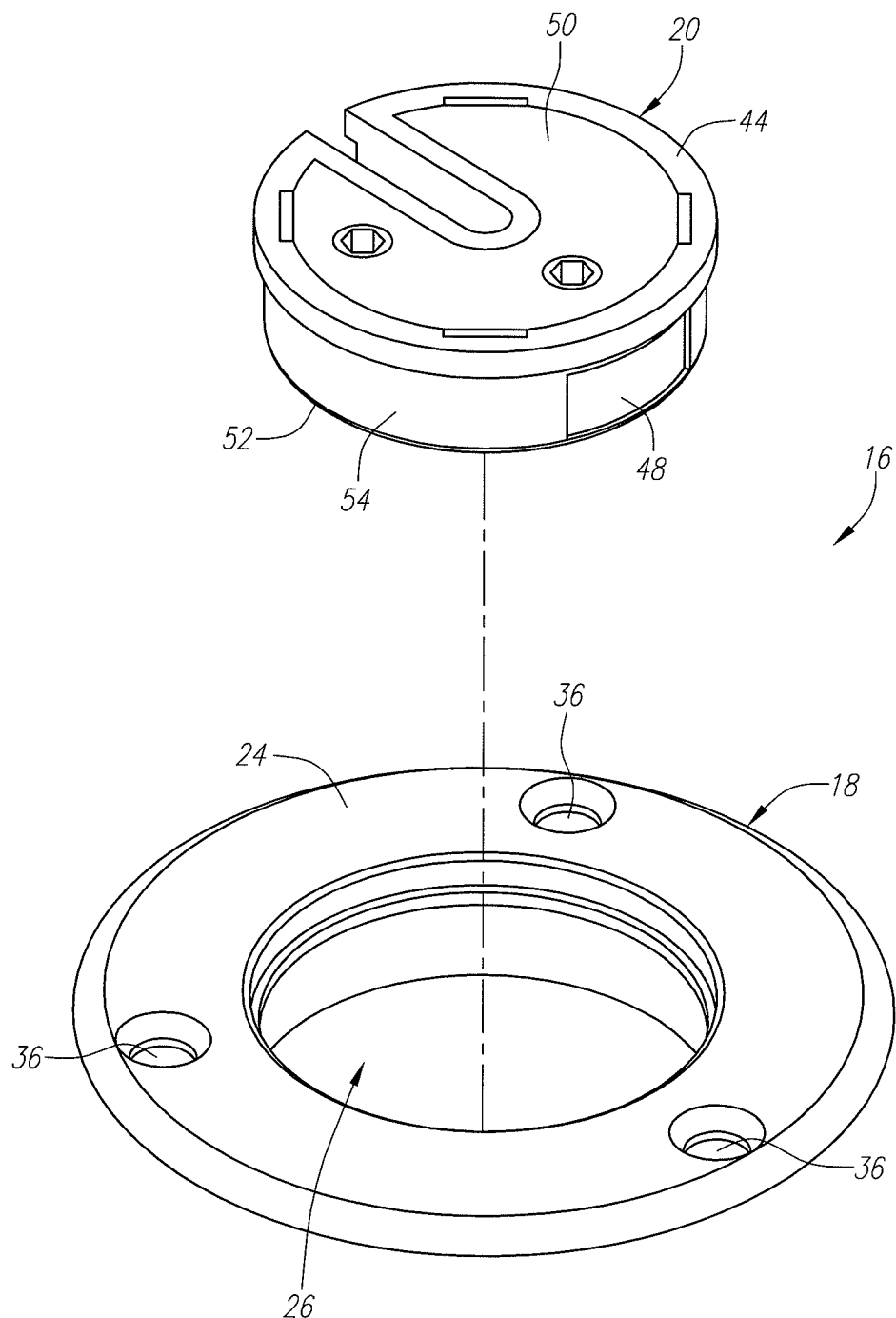
FIG. 2 is an exploded view of a burr hole plug constructed in accordance with one embodiment of the present inventions.
Figure 3:
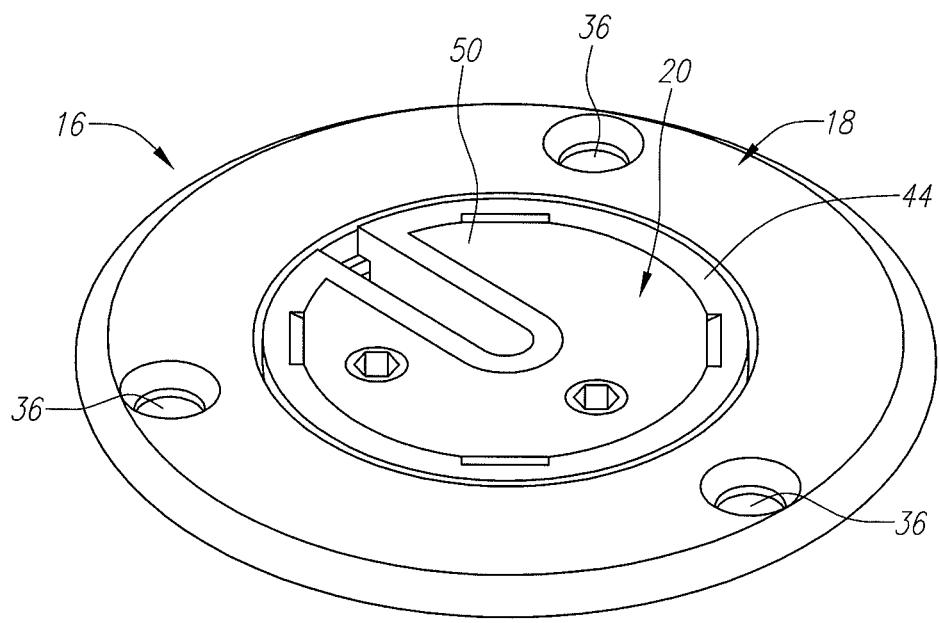
FIG. 3 is a top perspective view of the burr hole plug of FIG. 2.
Figure 4:
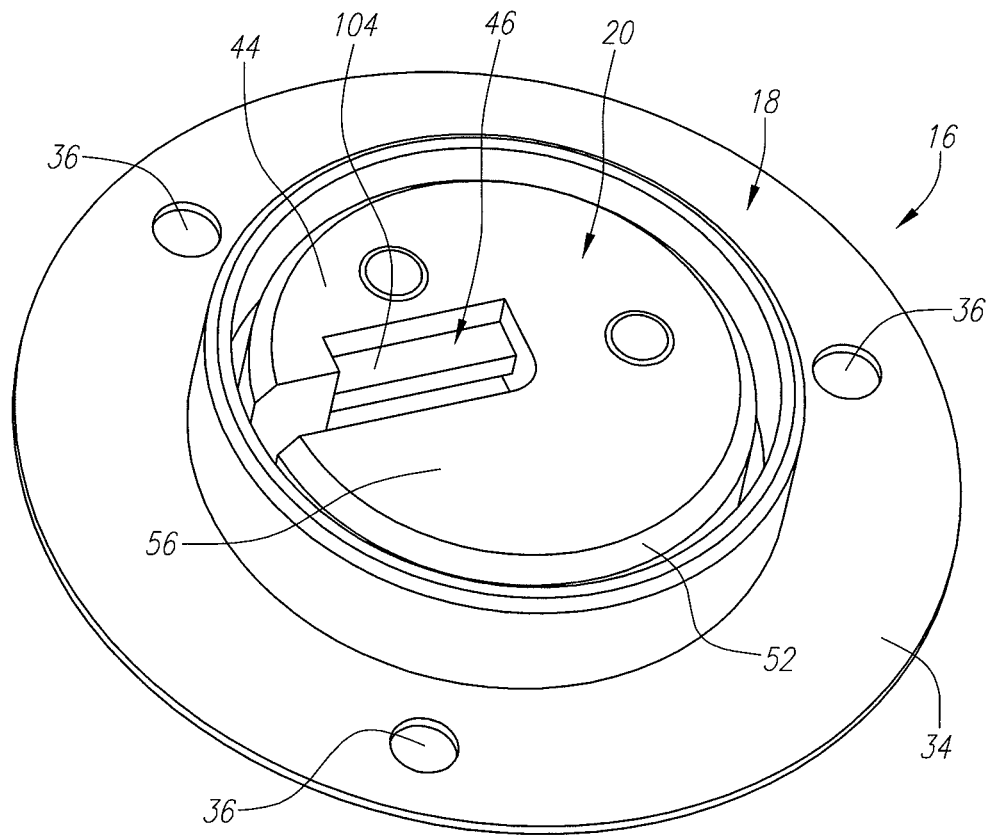
FIG. 4 is a bottom perspective view of the burr hole plug of FIG. 2, particularly showing stimulation lead and plug base clamping mechanisms in their fully recessed positions.

Turning first to FIG. 1, an exemplary DBS system 10 constructed in accordance with one embodiment of the present inventions is shown implanted within a patient for the treatment of a debilitating disease such as, Parkinson's disease, dystonia, essential tremor, seizure disorders, obesity, depression, etc. The system 10 comprises a stimulation lead 12 implanted within the parenchyma of the brain 2 of a patient 1 in order to position electrodes 14 carried by the distal end of the stimulation lead 12 adjacent a target tissue region 3, such as a deep brain structure of the patient (e.g., the ventrolateral thalamus, internal segment of globus pallidus, substantia nigra pars reticulate, subthalamic nucleus, or external segment of globus pallidus). Thus, electrical stimulation energy can be conveyed from the electrodes 14 to the target tissue region 3 to treat the disease. As can be seen, the stimulation lead 12 is introduced into the head 4 of the patient 1 via a burr hole 5 formed in the cranium 6 of the patient 1. In alternative embodiments, multiple stimulation leads (not shown) may be used, all of which may be located within the head 4 of the patient 1 via the same burr hole 5.

To secure the stimulation lead 12 (or leads), the system 10 further comprises a burr hole plug 16 mounted to the cranium 6 around the burr hole 5 of the patient 1. The stimulation lead 12 extends from the burr hole 5, through the burr hole plug 16, to a location external to the cranium 6. Details discussing the structure and function of various embodiments of the burr hole plug 16 will be discussed in further detail below.

The DBS system 10 further comprises a neurostimulator 17, such as an implantable pulse generator (IPG), radio frequency (RF) receiver-stimulator, or any other device coupled to and capable of delivering electrical stimulation energy to the stimulation lead 12 in a controlled and therapeutic manner. The neurostimulator 17 may be generally implanted in a surgically-made pocket in the torso of the patient (e.g., the chest or shoulder region). The neurostimulator 17 may, of course, also be implanted in other locations of the patient's body. The DBS system 10 further comprises a lead extension 19, which may be suitably connected to the proximal end of the stimulation lead 12 and subcutaneously advanced underneath the scalp 7 of the patient 1 to the neurostimulator implantation site, thereby facilitating the location of the neurostimulator 17 away from the exit point of the stimulation lead 12 (i.e., the burr hole 5). In alternative embodiments, the neurostimulator 17 may be directly implanted on or within the cranium 6 of the patient 1, as described in U.S. Pat. No. 6,920,359, which is expressly incorporated herein by reference. In this case, the lead extension 19 may not be needed. After implantation, the neurostimulator 17 is used to provide the therapeutic stimulation under control of the patient 1. The system 10 may include external components, such as a patient handheld programmer, a clinician programming station, and an external charger (all not shown), the details of which will not be described herein for purposes of brevity.

In should be understood that, while the invention lends itself well to applications in DBS, the invention, in its broadest aspects, may not be so limited. For example, the stimulation lead 12 (or leads) can be delivered within regions of the brain other than a deep brain structure, e.g., within or on the surface of the cerebral cortex. In addition, electrical leads, other than stimulation leads, may be delivered within the head 4 of the patient 1. For example, an electrical recording lead can be delivered into the head 4 of the patient 1 via the burr hole 5 to sense brain signals, either alone or in conjunction with a stimulation lead. Further, elongated medical devices other than electrical leads; for example, drug delivery catheters or needles, may be delivered into the head 4 of the patient 1 via the burr hole 5. Thus, it can be appreciated that the burr hole plugs described herein can be used with any elongated medical device intended to be delivered through a burr hole 5 within the cranium 6 of a patient 1 for any therapeutic and/or diagnostic purpose.

Referring now to FIGS. 2-10, one embodiment of the burr hole plug 16 will be described. The burr hole plug 16 generally comprises a plug base (or shell) 18 configured for being fixably mounted about a burr hole, and a retainer 20 configured for being mounted within the plug base 18 to secure a stimulation lead extending through the burr hole. An optional cap (not shown) can be mounted to the plug base 18 over the retainer 20 in order to further secure the stimulation lead 12 (or leads). The burr hole plug 16 further comprises a plurality of fasteners (not shown) for mounting the plug base 18 to the cranium of the patient. Any of the components of the burr hole plug 16 may be composed of a suitable hard biocompatible material, such as titanium, stainless steel (e.g., MP35N), alloys, or hard polymers (e.g., a high durometer silicone, polyurethane, or polyethertheterketone (PEEK)).

Figure 8:
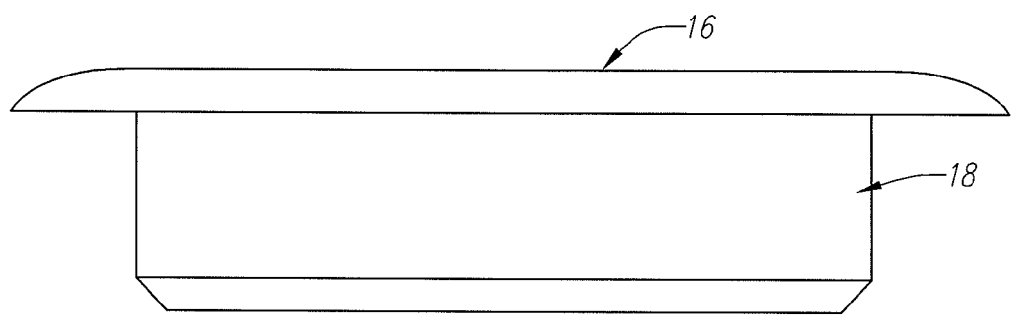
FIG. 8 is a side view of the burr hole plug of FIG. 2.
Figure 11:
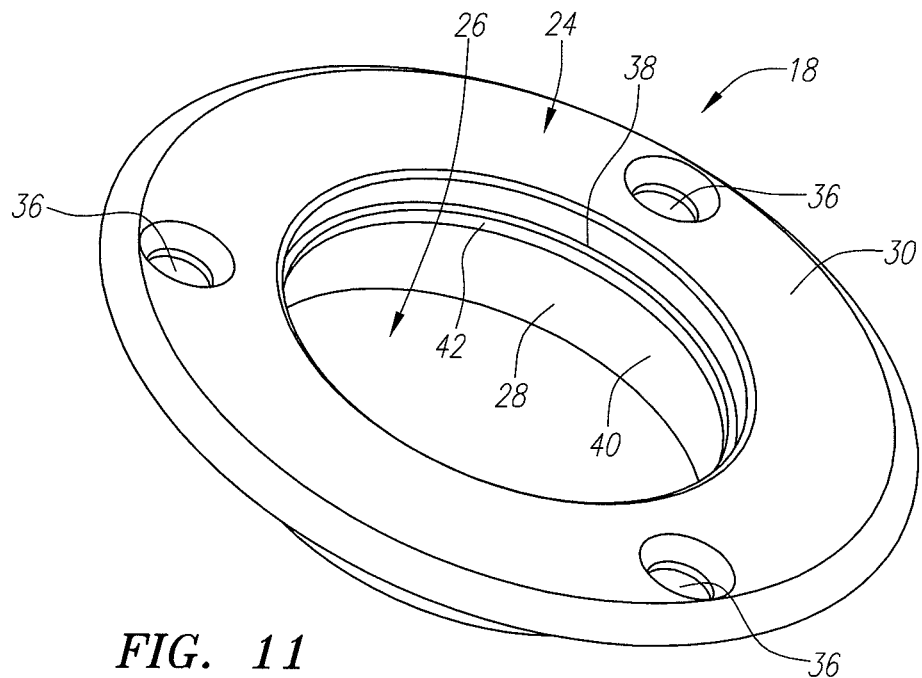
FIG. 11 is a top perspective view of a plug base used in the burr hole plug of FIG. 2.
Figure 12:
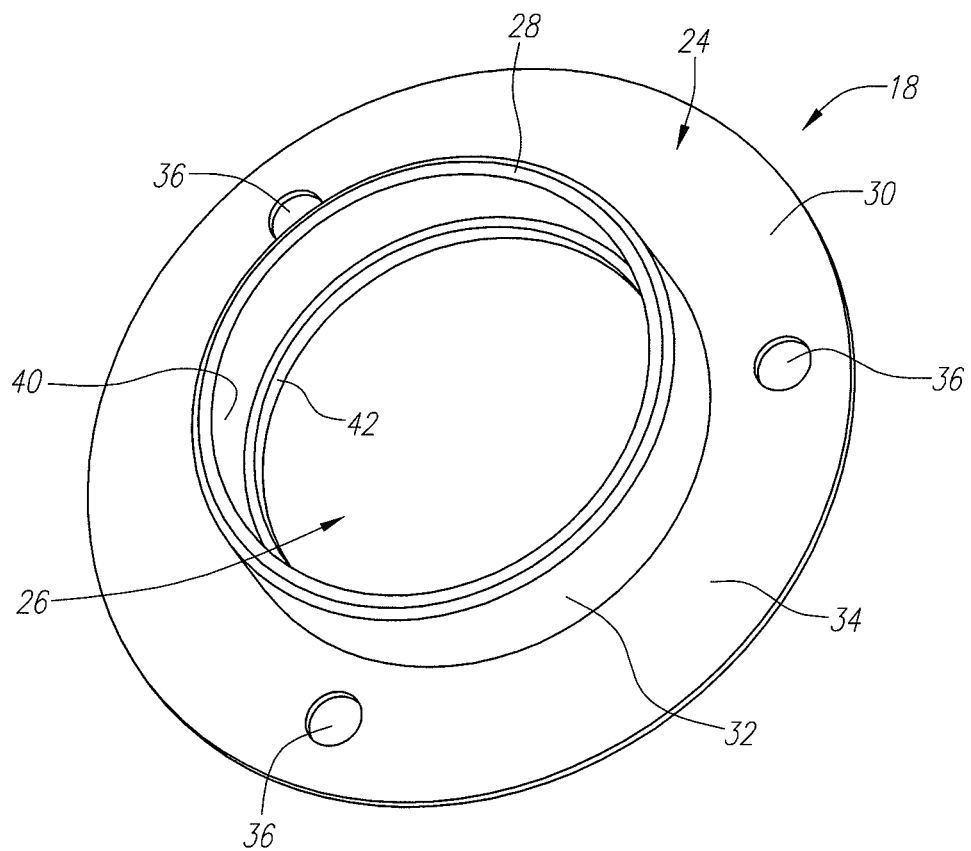
FIG. 12 is a bottom perspective view of a plug base used in the burr hole plug of FIG. 2.

Referring further to FIGS. 11 and 12, the plug base 18 includes a closed ring-shaped body 24 and an aperture 26 through which the stimulation lead exiting from the burr hole may pass. The profile of the ring-shaped body 24 is preferably minimized as much as possible, such that the plug base 18 does not noticeably protrude from the cranium underneath the scalp of the patient. To this end, the plug base 18 conventionally comprises an inner cylindrical flange 28 configured for being disposed within the cranial burr hole, and an outer circular flange 30 orthogonally extending radially outward from the top of the inner flange 28, such that the outer flange 30 is configured to reside outside of the cranial burr hole on top of the cranium when the inner flange 28 is disposed within the cranial burr hole. As a result, the height of the profile of the burr hole plug 16 above the cranial burr hole is equal to the thickness of the outer flange 30 (as best shown in FIG. 8), thereby reducing the visibility of the burr hole plug 16 below the patient's scalp. The size of the inner flange 28 preferably matches the size of the cranial burr hole, such that an outer surface 32 of the inner flange 28 firmly engages the cranial burr hole. In this case, the greatest dimension (in this case, its diameter) of the inner flange 28 may be in the range of 10 mm-20 mm. The bottom surface 34 of the ring-shaped body 24 may optionally be concave (not shown) in order to match the curvature of a typical cranium.

In the illustrated embodiment, the plug base 18 is permanently anchored to the cranium of the patient. To this end, the plug base 18 includes three fastening holes 36 formed within the outer flange 30 of the ring-shaped body 24 for respectively receiving anchoring fasteners (not shown), such as, e.g., screws, pins, spikes, tabs, or buttons. Alternatively, other means of anchoring the plug base 18 to the cranium of the patient, such as, e.g., adhesion, can be used. Relief structures (not shown) may be added to the bottom surface 34 of the ring-shaped body 24 and the outer surface 32 of the inner flange 28 to prevent rotational movement between the plug base 18 and the burr hole prior to permanent anchoring to the cranium. Such relief structures may include, e.g., a rough sandpaper-like surface, notches, bumps, horizontal or vertical ribs or threads, etc.

The plug base 18 also comprises an inner annular ledge 38 configured for supporting the retainer 20 when mounted within the plug base aperture 26. In particular, the annular ledge 38 is disposed on the inner surface 40 of the inner flange 28, thereby preventing the retainer 20 from descending too far into the burr hole when mounted within the aperture 26. The plug base 18 further comprises an annular ridge 42 extending radially inward from the inner surface 40 of the inner flange 28 just below the annular ledge 38. As will be described in further detail below, the annular ridge 42 allows the retainer 20 to be axially secured within the plug base aperture 26. In the illustrated embodiment, the ring-shaped body 24 is closed, thereby maximizing the durability of the plug base 18. In one alternative embodiment, the plug base 18 may include an open slot (not shown) configured for laterally receiving the stimulation lead. This permits the plug base 18 to be mounted to the cranium around the burr hole after the stimulation lead has been inserted through the burr hole and into the brain tissue by simply sliding the stimulation lead through the slot as the plug base 18 is moved into place. In another alternative embodiment, the plug base 18 may comprise at least two body portions (not shown) that can be integrated together when mounting to the burr hole.

Referring further to FIGS. 13-24, the details of the retainer 20 will now be described. As clearly shown in FIG. 13, the retainer 20 comprises a retainer support 44 configured for being mounted within the plug base aperture 26 (shown in FIGS. 11 and 12), a lead clamping mechanism 46 mounted to the retainer support 44 and configured for securing the stimulation lead, a base clamping mechanism 48 mounted to the retainer support 44 and configured for securing the retainer 20 within the plug base 18, and a lid 50 configured for containing the clamping mechanisms 46, 48 within the retainer support 44.

Figure 22:
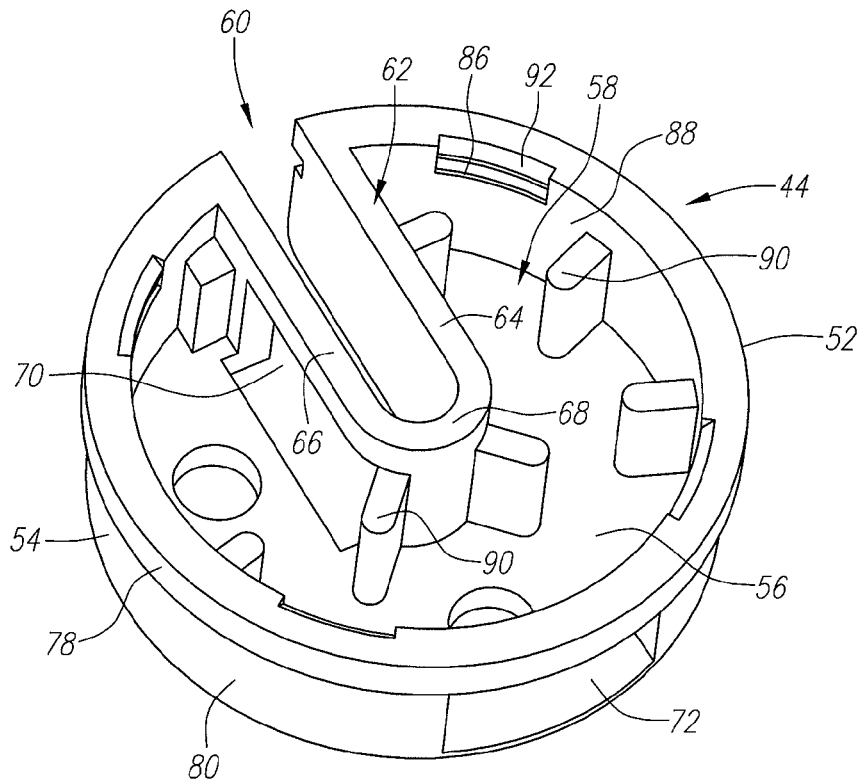
FIG. 22 is a top perspective view of a retainer support used in the retainer of FIG. 14.
Figure 23:
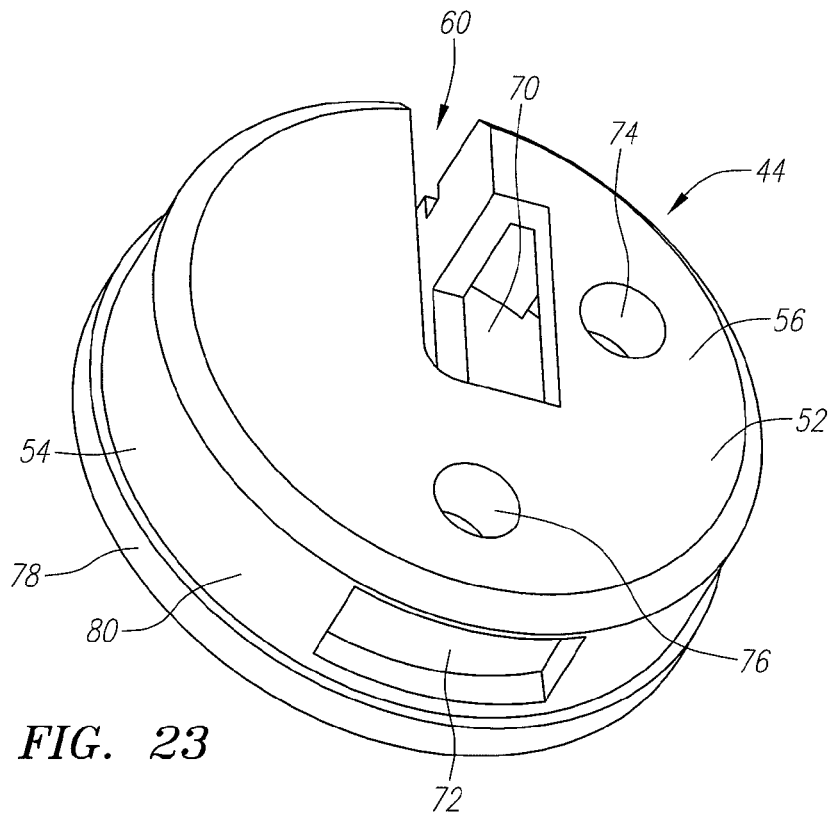
FIG. 23 is a bottom perspective view of a retainer support used in the retainer of FIG. 14.

As best shown in FIGS. 22 and 23, the retainer support 44 comprises a disk-shaped housing 52 having an outer annular or cylindrical sidewall 54, a bottom floor 56, and a cavity 58 in which the clamping mechanisms 46, 48 are disposed. The retainer support 44 further comprises an open lead slot 60 formed in the retainer housing 52 for laterally receiving the stimulation lead, thereby allowing the retainer 20 to be mounted within the plug base aperture 26 after the stimulation lead has been introduced through the burr hole. In the illustrated embodiment, the lead slot 60 radially extends through the center of the retainer housing 52. The lead slot 60 may alternatively terminate at or short of the center of the retainer housing 52 or may be offset from the center of the retainer housing 52. The retainer housing 52 further comprises an inner U-shaped sidewall 62 that extends around the lead slot 60. In particular, the inner sidewall 62 has two straight sidewall portions 64, 66 that extend along opposite sides of the lead slot 60, and a curved sidewall portion 68 that connects the straight sidewall portions 64, 66 at the end of the lead slot 60.

The retainer support 44 further comprises a first opening 70 formed in one of the straight sidewall portions 64, 66 and a second opening 72 formed in the outer sidewall 54. As will be described in further detail below, the first and second openings 70, 72 respectively accommodate movement of the lead and base clamping mechanisms 46, 48. The retainer support 44 further comprises first and second holes 74, 76 formed through the bottom floor 56 of the retainer housing 52 to which certain elements of the lead and base clamping mechanisms 46, 48 are mounted, as will also be described in further detail below.

Figure 5:
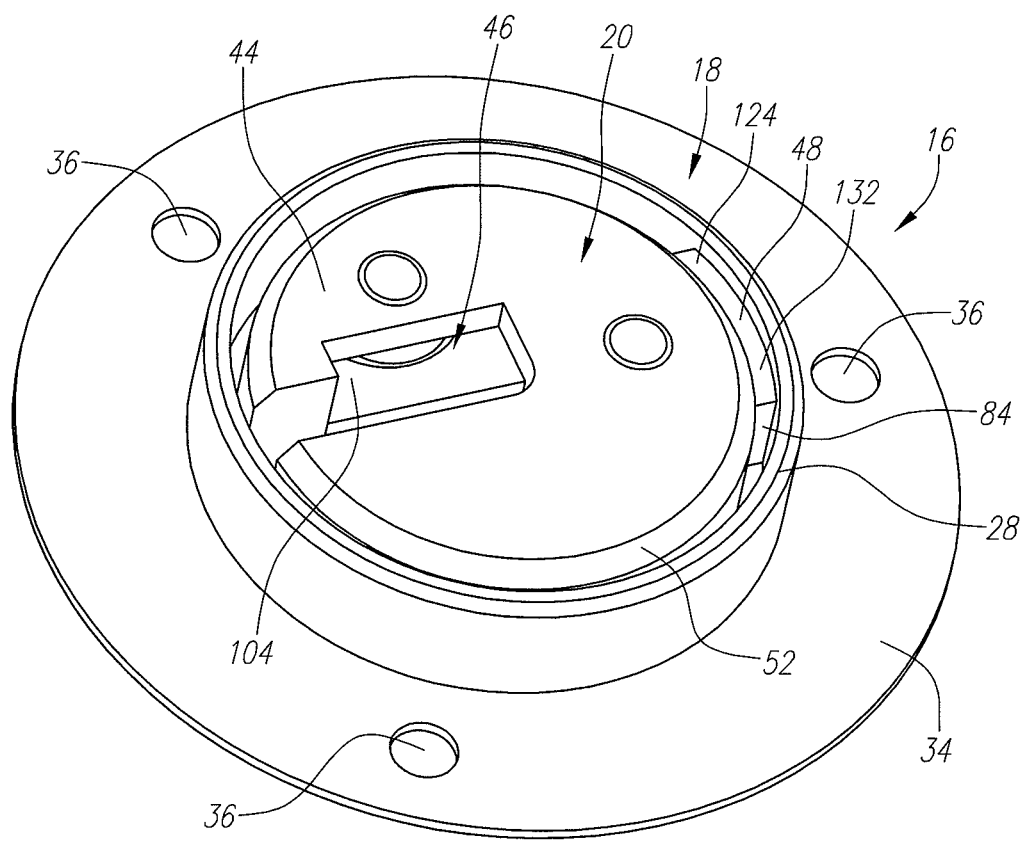
FIG. 5 is a bottom perspective view of the burr hole plug of FIG. 2, particularly showing stimulation lead and plug base clamping mechanisms in their fully deployed positions.
Figure 6:
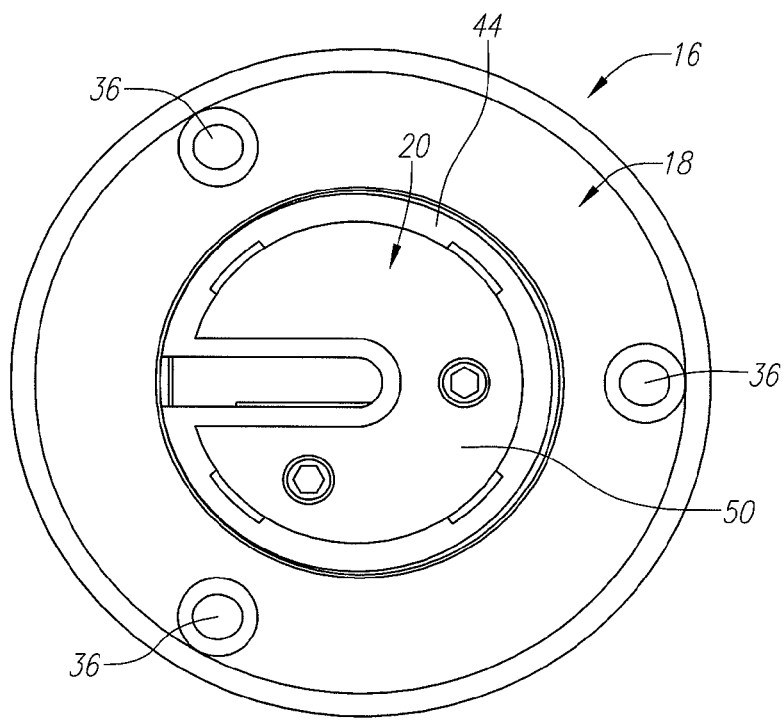
FIG. 6 is a top view of the burr hole plug of FIG. 2, particularly showing the stimulation lead clamping mechanism in its fully recessed position.
Figure 7:
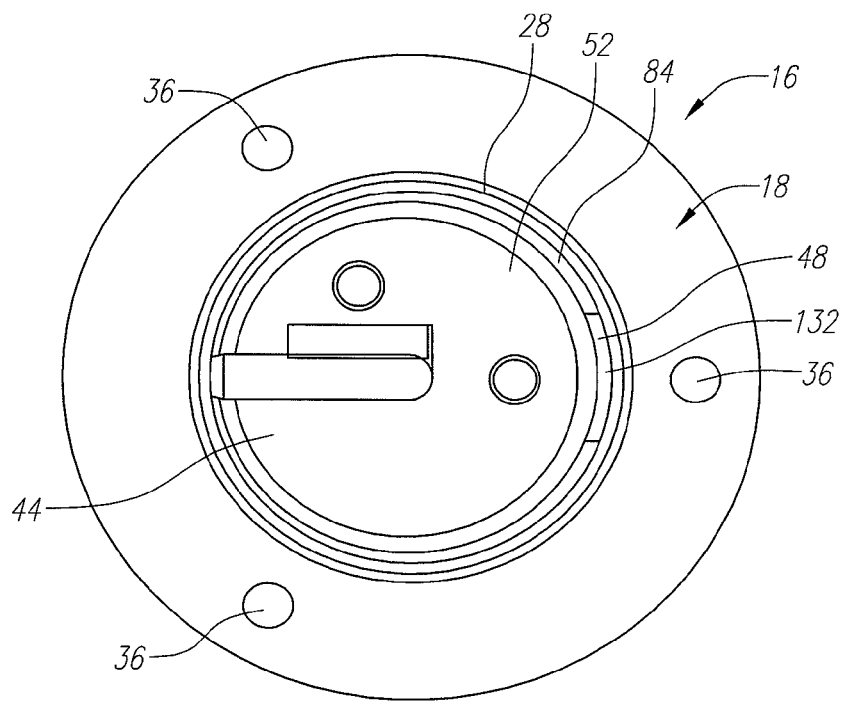
FIG. 7 is a bottom view of the burr hole plug of FIG. 2, particularly showing the stimulation lead clamping mechanism in its fully recessed position and the plug base clamping mechanism in its fully deployed position.
Figure 9:
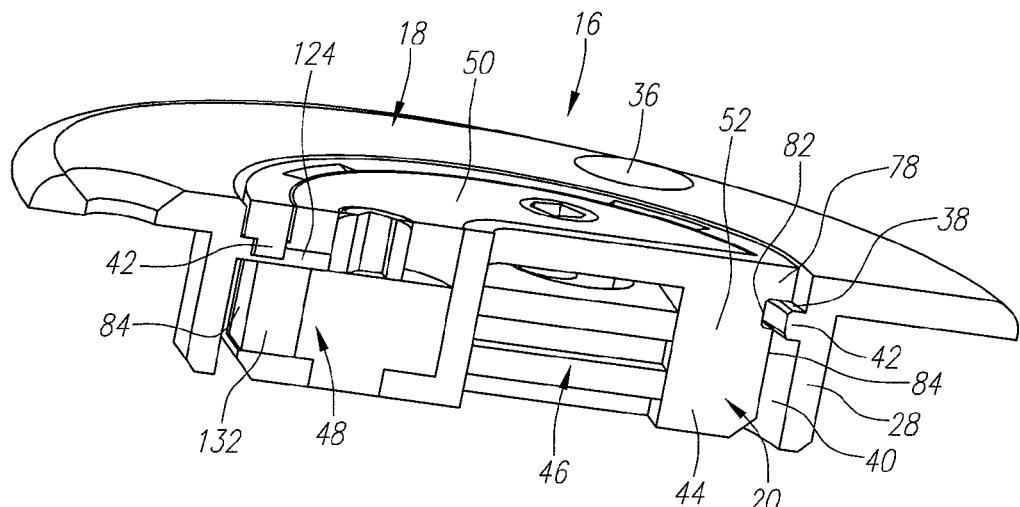
FIG. 9 is a cross-sectional perspective view of the burr hole plug of FIG. 2, particularly showing stimulation lead and plug base clamping mechanisms in their fully recessed positions.
Figure 10:
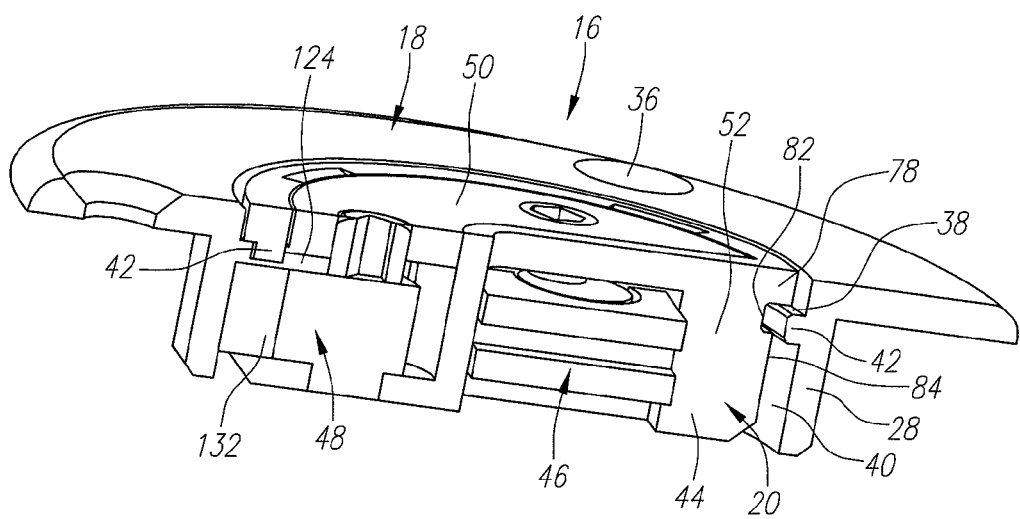
FIG. 10 is a cross-sectional perspective view of the burr hole plug of FIG. 2, particularly showing stimulation lead and plug base clamping mechanisms in their fully deployed positions.

The retainer support 44 further comprises an annular lip 78 formed at the top of, and extending radially outward from the outer surface 80 of, the outer sidewall 54. Thus, as best shown in FIGS. 9 and 10, when the retainer 20 is mounted within the plug base 18, the lower surface of the annular lip 78 (also shown in FIGS. 14 and 15) rests on the upper surface of the annular ledge 38 (also shown in FIG. 11) formed on the inner surface 40 of the inner plug base flange 28, thereby restraining axial movement of the retainer 20 into the cranial burr hole. In this configuration, the top of the retainer 20 is preferably flush with the top of the plug base 18. The retainer support 44 also comprises an annular recess 82 that circumferentially extends around a portion of the outer surface 80 of the outer sidewall 54 just below the annular lip 78. As will be described in further detail below, the annular recess 82 (also shown in FIG. 14) receives the annular ridge 42 located on the inner surface 40 of the inner plug base flange 28 to axially secure the retainer 20 within the plug base 18. In the illustrated embodiment, the annular recess 82 circumferentially extends 180 degrees around the outer sidewall 54. As best shown in FIGS. 5, 9, and 10, an annular aperture 84 is formed between the outer sidewall 54 of the retainer housing 52 and the inner flange 28 of the plug base 18 when the retainer 20 is mounted within the plug base 18. In this manner, the retainer 20 may freely spin within the plug base 18 until the base clamping mechanism 48 is actuated, as will be described in further detail below.

Figure 24:
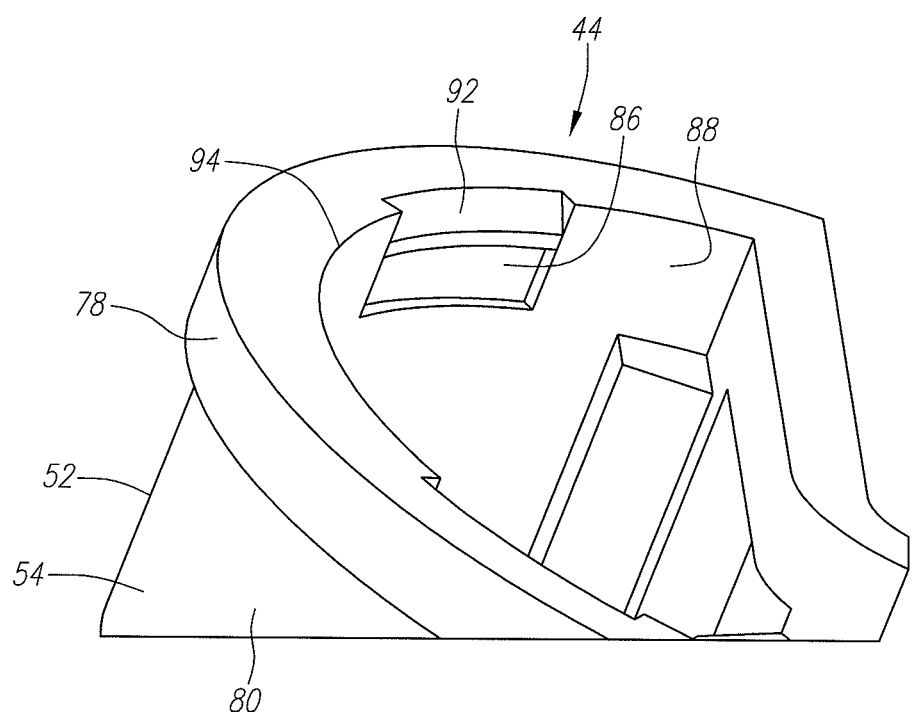
FIG. 24 is a close-up view of the lid-locking recesses and lid pop-out recesses formed in the retainer support of FIG. 22.

The retainer support 44 is configured for receiving the lid 50 in an interference arrangement, and in particular, a snap-fit arrangement. To this end, the retainer support 44 further comprises a plurality of lid locking recesses 86 (as best shown in FIG. 24) formed in the inner surface 88 of the outer sidewall 54. As will be described in further detail below, the lid locking recesses 86 can receive corresponding lid locking ridges (described below) for facilitating mounting of the lid 50 to the retainer housing 52. Alternatively, the lid 50 can be secured to the retainer housing 52 using a threaded arrangement or bonding means, such as heat welding. The retainer support 44 further comprises a plurality of tab-like ledges 90 extending along the bottom floor 56 from the outer sidewall 54 and the inner sidewall 62. Each of the ledges 90 has a height that is flush with the lid locking recesses 86, such that the ledges 90 prevent the movement of the lid 50 past the lid locking recesses 86, thereby facilitating mounting of the lid 50 onto the retainer housing 52. The retainer support 44 further comprises a plurality of corresponding lid pop-out recesses 92 (as best shown in FIG. 24) located at a top inner edge 94 of the outer sidewall 54 such that a tool (not shown) can be inserted into one of the lid pop-out recesses 92 to remove the previously mounted lid 50 from the retainer housing 52.

Figure 13:
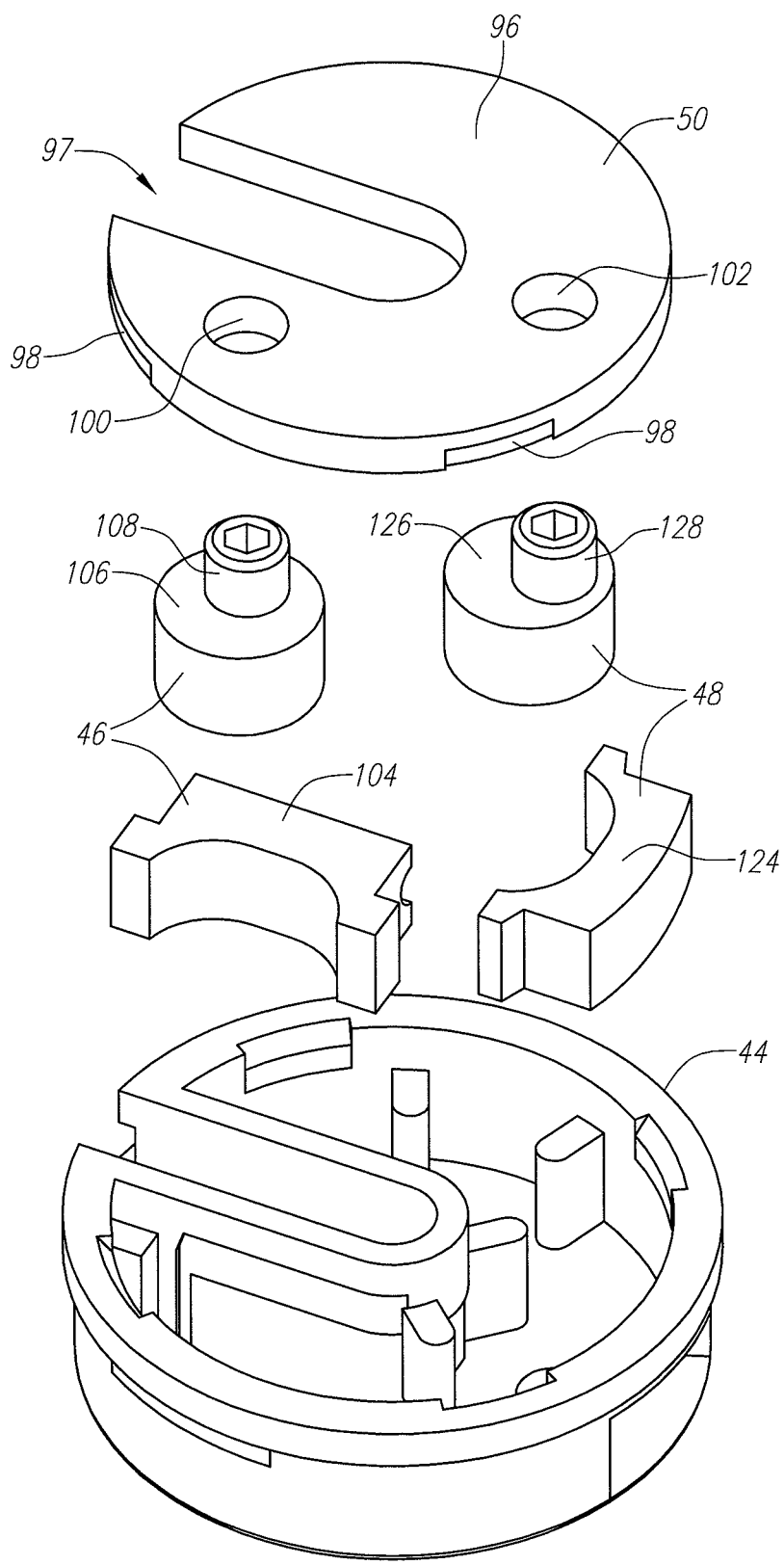
FIG. 13 is an exploded view of a retainer used in the burr hole plug of FIG. 2.
Figure 14:
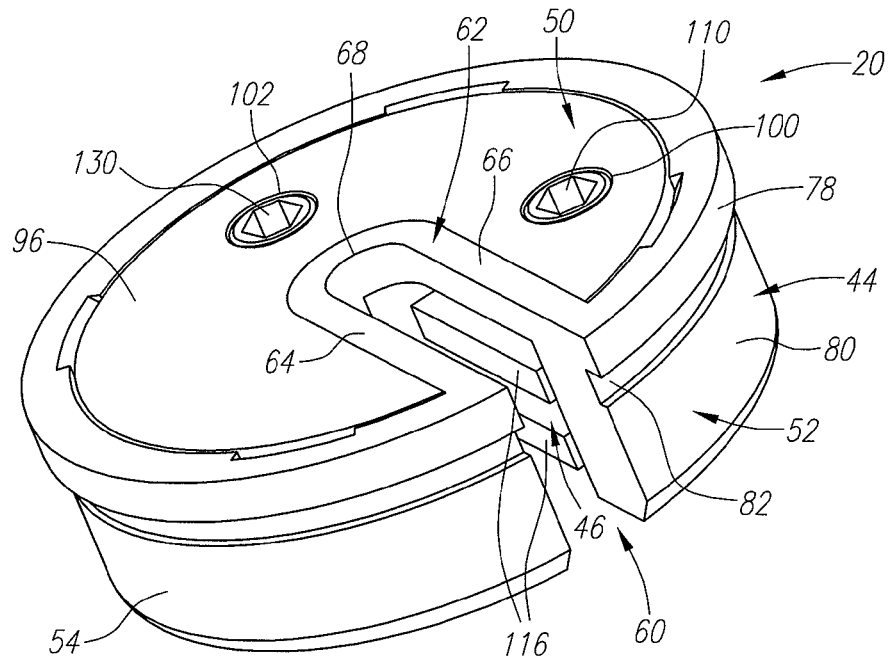
FIG. 14 is a top perspective view of the retainer of FIG. 13.
Figure 15:
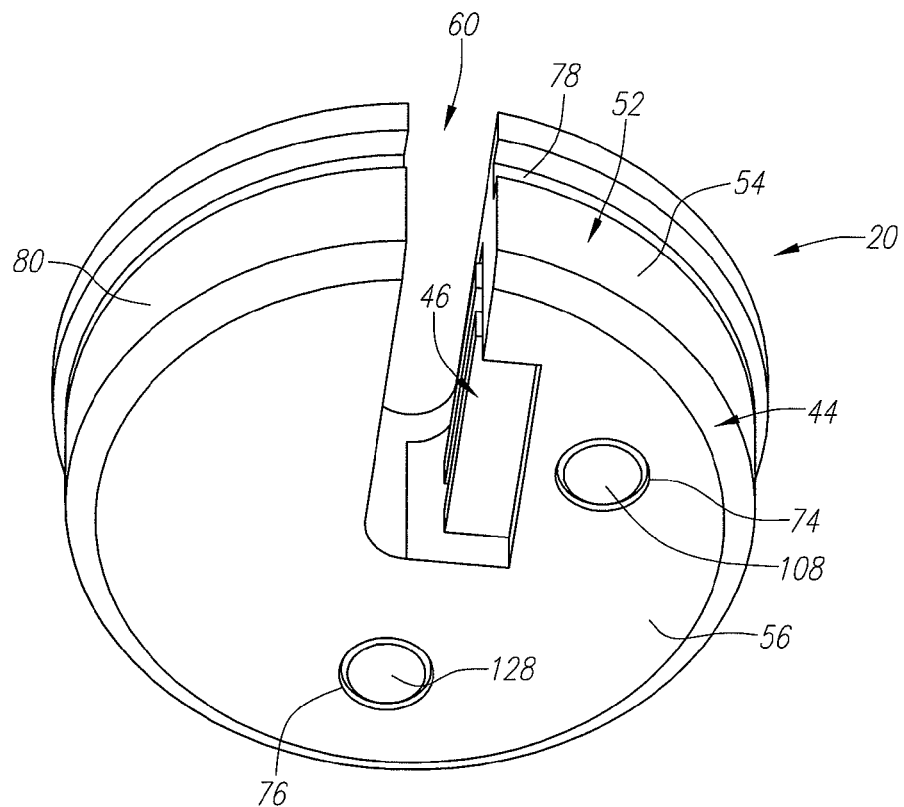
FIG. 15 is a bottom perspective view of the retainer of FIG. 13.
Figure 16:
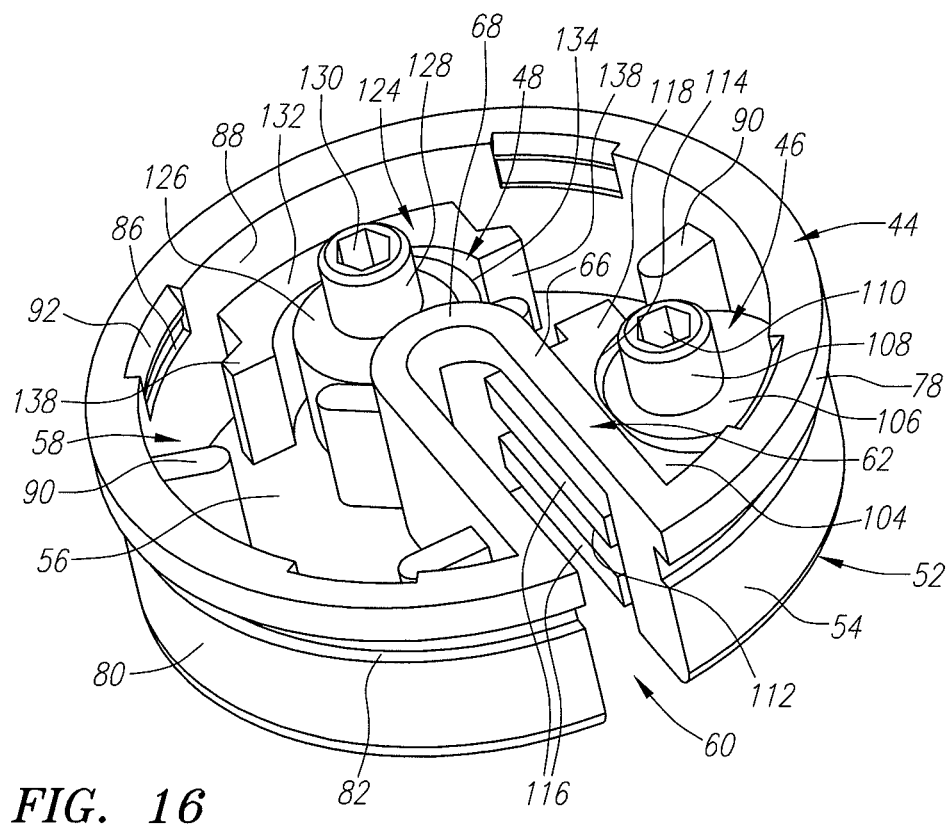
FIG. 16 is a top perspective view of the retainer of FIG. 14 with the lid removed, particularly showing the stimulation lead and plug base clamping mechanisms in their fully recessed positions.
Figure 17:
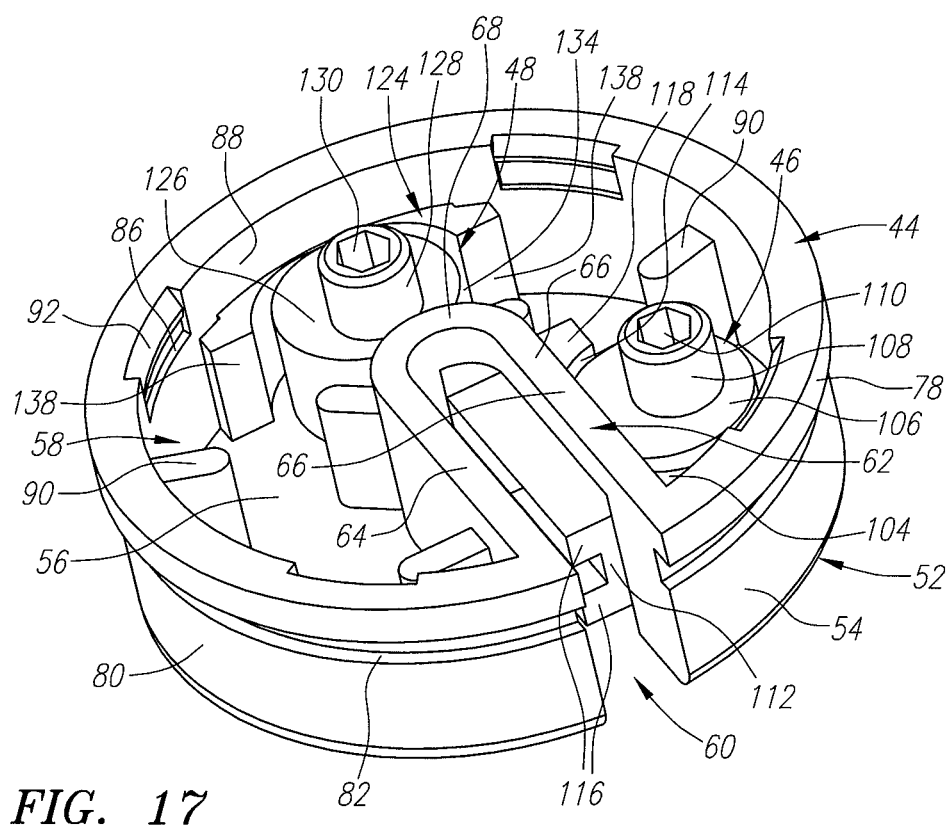
FIG. 17 is a top perspective view of the retainer of FIG. 14 with the lid removed, particularly showing the stimulation lead and plug base clamping mechanisms in their fully deployed positions.
Figure 18:
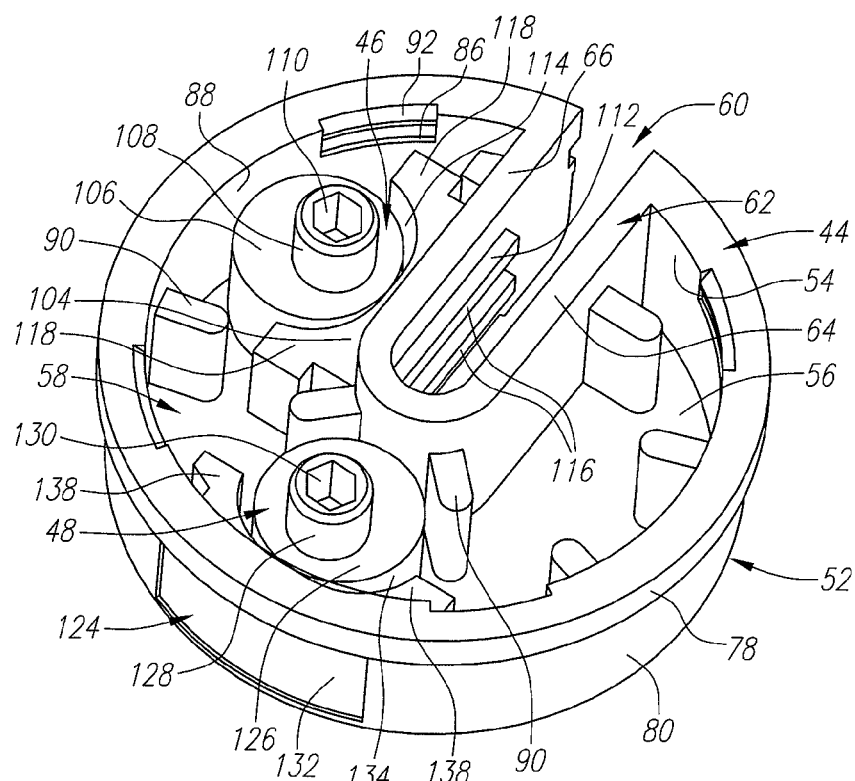
FIG. 18 is another top perspective view of the retainer of FIG. 14 with the lid removed, particularly showing the stimulation lead and plug base clamping mechanisms in their fully recessed positions.
Figure 19:
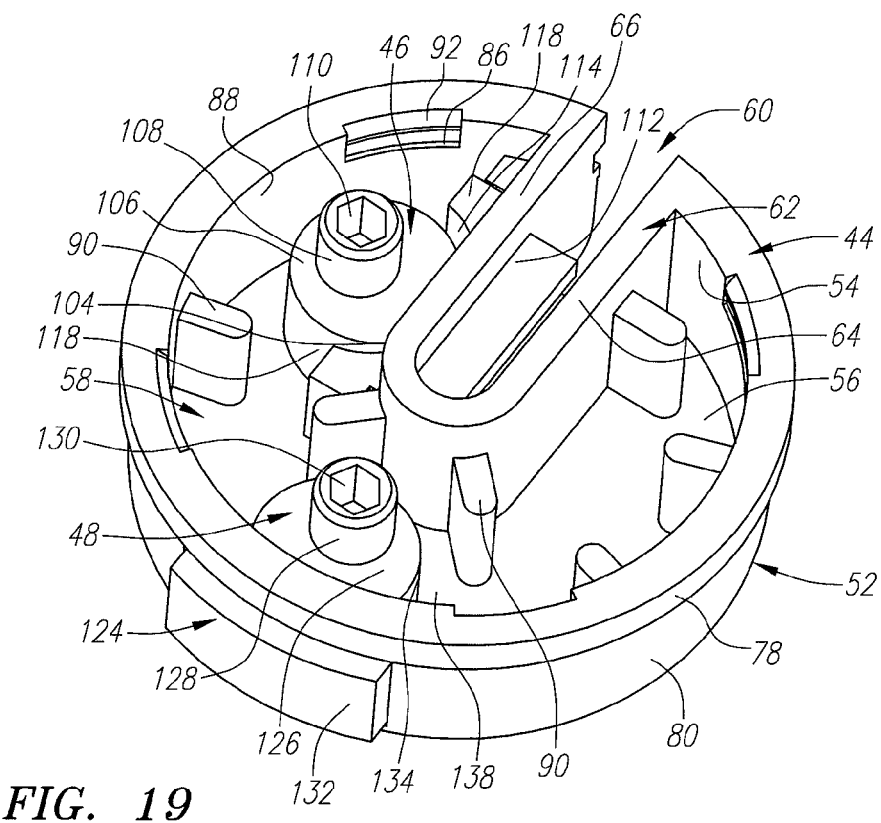
FIG. 19 is another top perspective view of the retainer of FIG. 14 with the lid removed, particularly showing the stimulation lead and plug base clamping mechanisms in their fully deployed positions.
Figure 20:
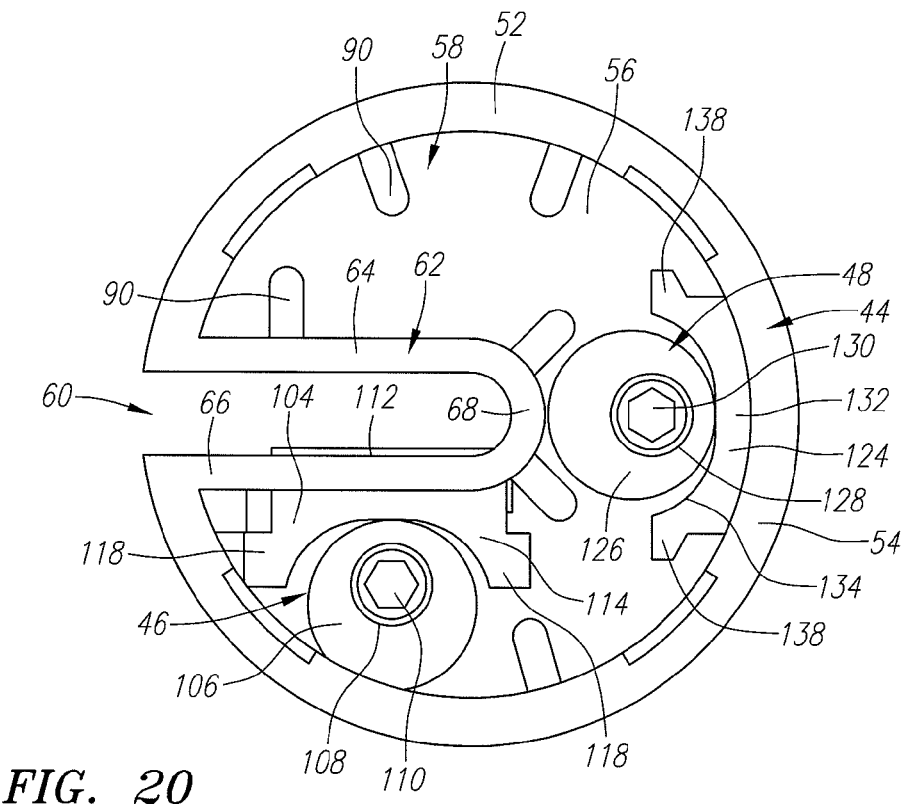
FIG. 20 is a top view of the retainer of FIG. 14 with the lid removed, particularly showing the stimulation lead and plug base clamping mechanisms in their fully recessed positions.
Figure 21:
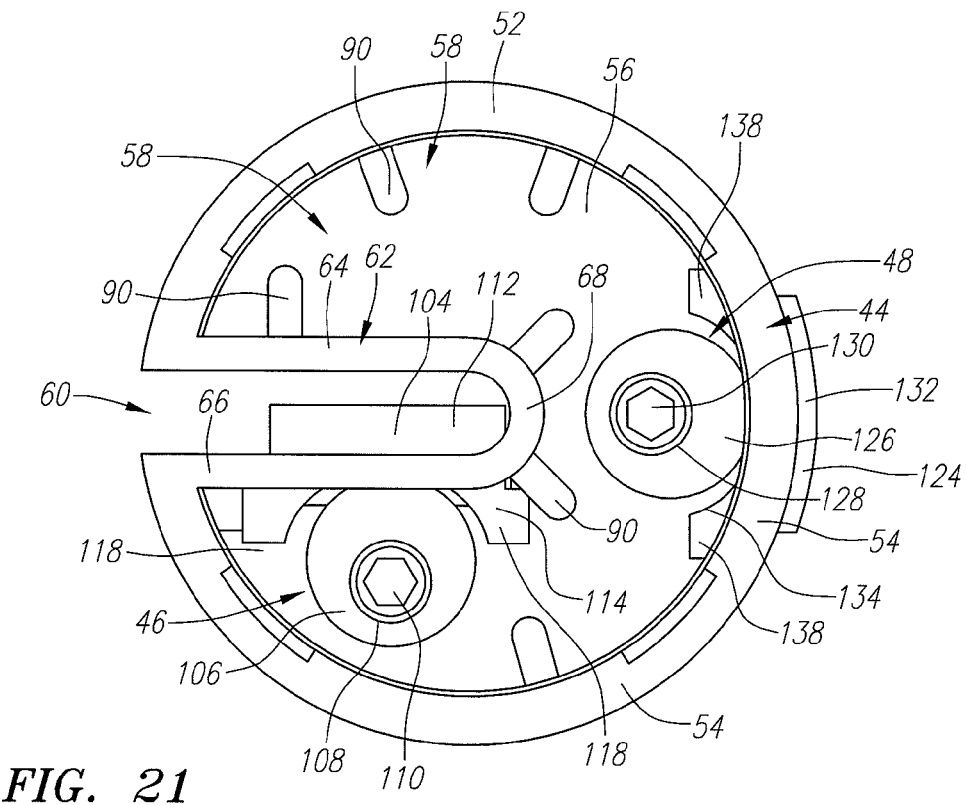
FIG. 21 is a top view of the retainer of FIG. 14 with the lid removed, particularly showing the stimulation lead and plug base clamping mechanisms in their fully deployed positions.

As best shown in FIG. 13, the lid 50 comprises a disk-shaped flange 96 having a diameter substantially equal to the inner diameter of the outer sidewall 54 of the retainer housing 52. The lid 50 further comprises a slot 97 formed within the disk-shaped flange 96 that accommodates the inner sidewall 62 of the retainer housing 52 (shown in FIG. 22), and a plurality of ridges 98 (in this case four) equally spaced around the edge of the disk-shaped flange 96 for being received within the lid locking recesses 86 formed around the inner surface 88 of the outer sidewall 54 of the retainer housing 52 (shown in FIG. 24). The lid 50 further comprises first and second holes 100, 102 formed through the disk-shaped flange 96 for providing access to the clamping mechanisms 46, 48, as will be described in further detail below.

Referring specifically to FIGS. 16-21, the lead clamping mechanism 46 comprises a movable clamping element 104 slidably disposed on the bottom floor 56 of the retainer housing 52, a cam 106 slidably engaged with the movable clamping element 104, and a cam shaft 108 on which the cam 106 is affixed. The cam shaft 108 is rotatably mounted within the first hole 74 formed in the bottom floor 56 of the retainer housing 52, such that it can be rotated about a fixed axis to rotate the cam 106 relative to the retainer support 44. The end of the cam shaft 108 includes a tool engagement element 110 for engaging a tool (not shown) that can provide a mechanical advantage for rotation of the cam 106. In the illustrated embodiment, the tool engagement element 110 is hexagonal recess, thereby allowing rotation of the cam 106 using an Allen wrench. Other types of tool engagement elements, such as a slotted recess for receiving a flat head screwdriver, a crossed recess for receiving a Phillips screwdriver, or a bolt head for receiving an open-ended wrench, box-end wrench, or socket wrench can also be used. The location of the first hole 74 in the bottom floor 56 of the retainer housing 52 corresponds to the first hole 100 in the lid 50 (shown in FIG. 13), such that the end of the cam shaft 108 is seated within the first hole 100 to provide access to the tool engagement element 110.

The movable clamping element 104 comprises a clamping flange 112 configured for engaging the medical device, and a cam follower element 114 with which the cam 106 slidably engages. The cam 106 and cam shaft 108 are in an eccentric relationship, such that rotation of the cam shaft 108 about the fixed axis (i.e., the axis extending through the first hole 74) rotates the cam 106, which in turn, linearly translates the clamping flange 112 through the inner sidewall opening 70 and into the lead slot 60 as the cam 106 slidably engages the cam follower element 114. In the illustrated embodiment, the movable clamping element 104 can be displaced from a fully recessed position (FIGS. 4, 16, 18, and 20) to a fully deployed position (FIGS. 5, 17, 19, and 21) by rotating the cam shaft 108, and thus the cam 106, over an angle of 180 degrees from its initial angular position. However, other angular ranges can be used to displace the movable clamping element 104 between the fully recessed position and the fully deployed position. In the illustrated embodiment, the cam 106 is circular, although in alternative embodiments, can be other shapes, including oval or oblong.

In the illustrated embodiment, the clamping flange 112 includes two horizontal and parallel ridges 116 that facilitate retention of the stimulation lead. The movable clamping element 104 may be composed of a high friction material, such as a high durometer silicone or polyurethane, to maximize lead retention. The straight sidewall portion 64 on the other side of the lead slot 60 serves as a fixed clamping element with which the movable clamping element 104 cooperates to secure the stimulation lead therebetween. To ensure that the movable clamping element 104 smoothly slides out into the lead slot 60 without rotating, the width of the clamping flange 112 is slightly less than the width of the inner sidewall opening 70, such that the sides of the clamping flange 112 slidably engage the edges of the inner sidewall opening 70. The movable clamping element 104 further comprises a pair of opposing limiting tabs 118 outwardly extending away from the cam follower element 114. These limiting tabs 118 will abut the straight sidewall portion 66 to limit movement of the clamping element 104 through the inner sidewall opening 70, thereby preventing the clamping element 104 from falling into the lead slot 60.

The lead clamping mechanism 46 may include one or more spring elements (not shown) that urge the clamping element 104 back into its fully recessed position when the cam 106 is rotated to its initial position (i.e., 0 degree rotation). Alternatively, the lead clamping mechanism 46 may incorporate a ratchet feature or a one-way clutch feature (not shown) between the cam 106 and the cam follower element 114 to prevent loosening/slippage of the clamping element 104. An override feature, such as a push-button release (not shown) can be incorporated to allow the clamping element 104 to release the stimulation lead.

The base clamping mechanism 48 is similar to the lead clamping mechanism 46 in that it comprises a movable clamping element 124 slidably disposed on the bottom floor 56 of the retainer housing 52, a cam 126 slidably engaged with the movable clamping element 124, and a cam shaft 128 on which the cam 126 is affixed. The cam shaft 128 is rotatably mounted within the second hole 76 formed in the bottom floor 56 of the retainer housing 52, such that it can be rotated about a fixed axis to rotate the cam 126 relative to the retainer support 44. The end of the cam shaft 128 includes a tool engagement element 130 for engaging a tool (not shown) that can provide a mechanical advantage for rotation of the cam 126. In the illustrated embodiment, the tool engagement element 130 is hexagonal recess, thereby allowing rotation of the cam 126 using an Allen wrench. Other types of tool engagement elements, such as a slotted recess for receiving a flat head screwdriver, a crossed recess for receiving a Phillips screwdriver, or a bolt head for receiving an open-ended wrench, box-end wrench, or socket wrench can also be used. The location of the second hole 76 in the bottom floor 56 of the retainer housing 52 corresponds to the second hole 102 in the lid 50 (shown in FIG. 13), such that the end of the cam shaft 128 is seated within the second hole 102 to provide access to the tool engagement element 130.

The movable clamping element 124 comprises a clamping flange 132 configured for engaging the inner flange 28 of the plug base 18, and a cam follower element 134 with which the cam 126 slidably engages. The cam 126 and cam shaft 128 are in an eccentric relationship, such that rotation of the cam shaft 128 about the fixed axis (i.e., the axis extending through the second hole 76) rotates the cam 126, which in turn, linearly translates the clamping flange 132 through the outer sidewall opening 72 and into the annular space 84 (shown in FIGS. 5, 7, 9, and 10) formed between the retainer housing 52 and the inner flange 28 of the plug base 18 as the cam 126 slidably engages the cam follower element 134. In the illustrated embodiment, the movable clamping element 124 can be displaced from a fully recessed position (FIGS. 4, 9, 16, 18, and 20) to a fully deployed position (FIGS. 5, 10, 17, 19, and 21) by rotating the cam shaft 128, and thus the cam 126, over an angle of 180 degrees from its initial angular position. However, other angular ranges can be used to displace the movable clamping element 124 between the fully recessed position and the fully deployed position. In the illustrated embodiment, the cam 126 is circular, although in alternative embodiments, can be other shapes, including oval or oblong.

Notably, as best shown in FIG. 9, the upper surface of the clamping flange 132 slidably engages the lower surface of the annular ridge 42 formed on the inner flange 28 of the plug base 18, which in conjunction with the engagement between the annular recess 82 on the outer surface 80 of the outer sidewall 54 of the retainer housing 52 and the annular ridge 42 opposite the outer sidewall opening 72, prevents axial movement between the plug base 18 and the retainer 20. In the illustrated embodiment, the clamping flange 132 has an annular surface having a radius of curvature that matches the radius of curvature of the inner surface 40 of the inner flange 28 of the plug base 18, thereby maximizing contact, and thus the clamping force, between the clamping flange 132 and the plug base 18. The movable clamping element 124 may be composed of a high friction material, such as a high durometer silicone or polyurethane, to further maximize the clamping force applied to the plug base 18.

To ensure that the movable clamping element 124 smoothly slides out into the annular space 84 between the outer sidewall 54 of the retainer housing 52 and the inner flange 28 of the plug base 18, the width of the clamping flange 132 is slightly less than the width of the outer sidewall opening 72, such that the sides of the clamping flange 132 slidably engage the edges of the outer sidewall opening 72. The movable clamping element 104 further comprises a pair of opposing limiting tabs 138 outwardly extending away from the cam follower element 134. These limiting tabs 138 will abut the inner surface of the outer sidewall 54 to limit movement of the clamping element 124 through the outer sidewall opening 72, thereby preventing the clamping element 124 from falling into the annular space 84.

The base clamping mechanism 48 may include one or more spring elements (not shown) that urge the clamping element 124 back into its fully recessed position when the cam 126 is rotated to its initial position (i.e., 0 degree rotation). Alternatively, the base clamping mechanism 48 may incorporate a ratchet feature or a one-way clutch feature (not shown) between the cam 126 and the cam follower element 134 to prevent loosening/slippage of the clamping element 124. An override feature, such as a push-button release (not shown) can be incorporated to allow the clamping element 124 to release the stimulation lead.

Figure 25:
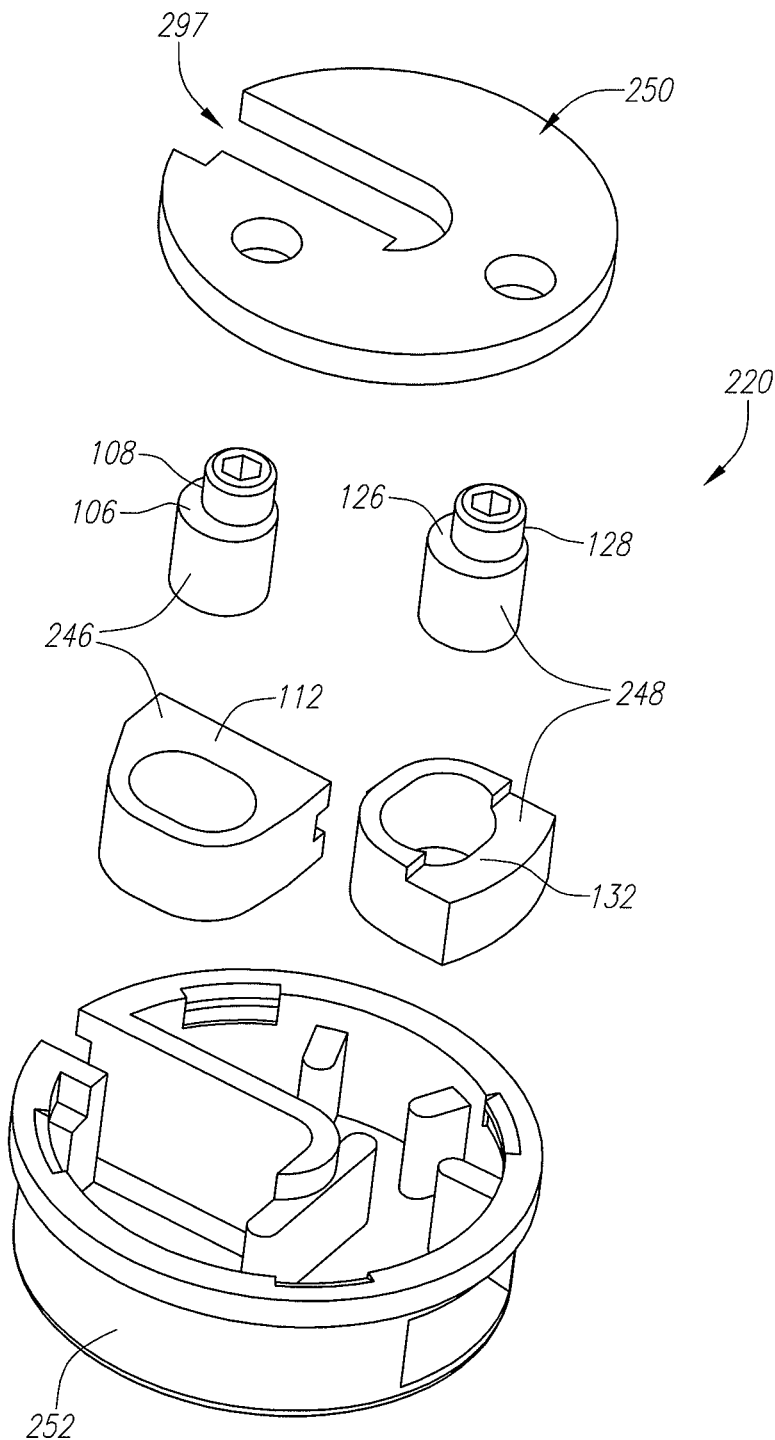
FIG. 25 is an exploded view of another retainer that can be used in the burr hole plug of FIG. 2.
Figure 26:
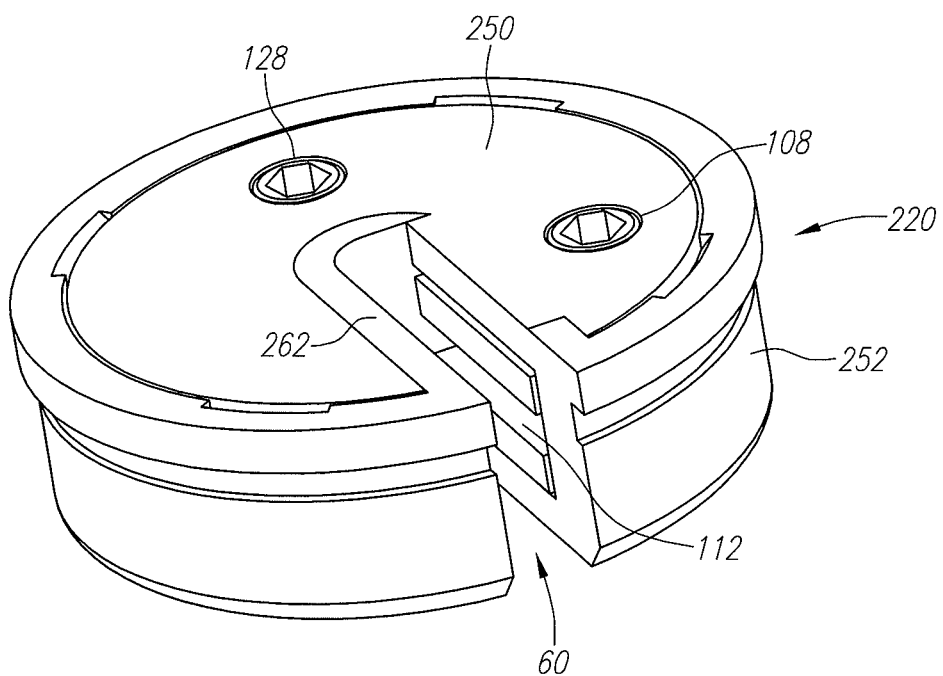
FIG. 26 is a top perspective view of the retainer of FIG. 25.
Figure 27:
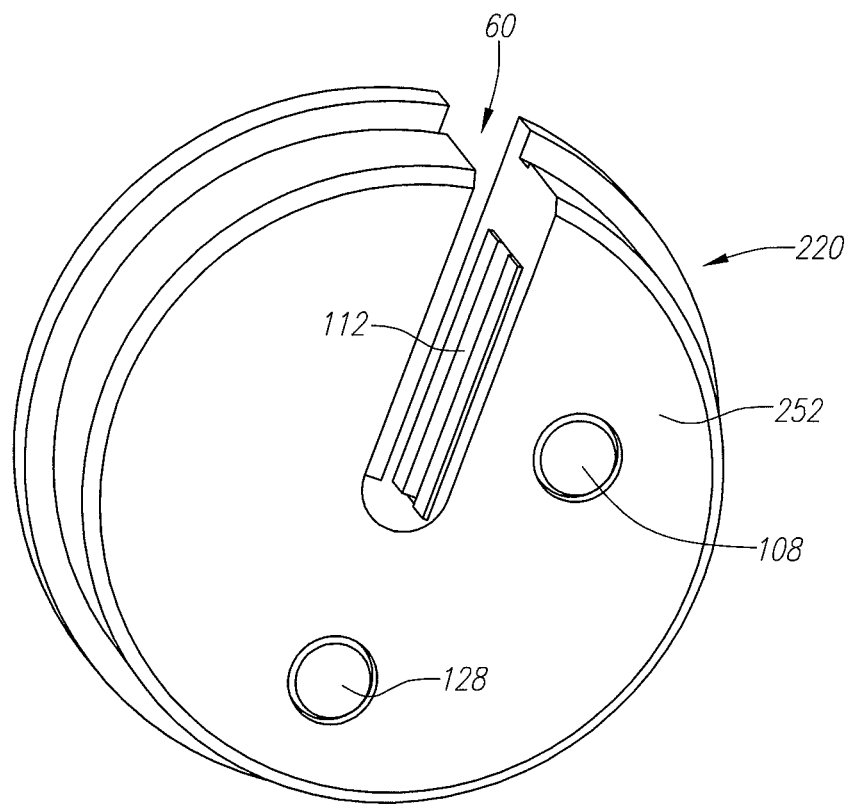
FIG. 27 is a bottom perspective view of the retainer of FIG. 25.
Figure 28:
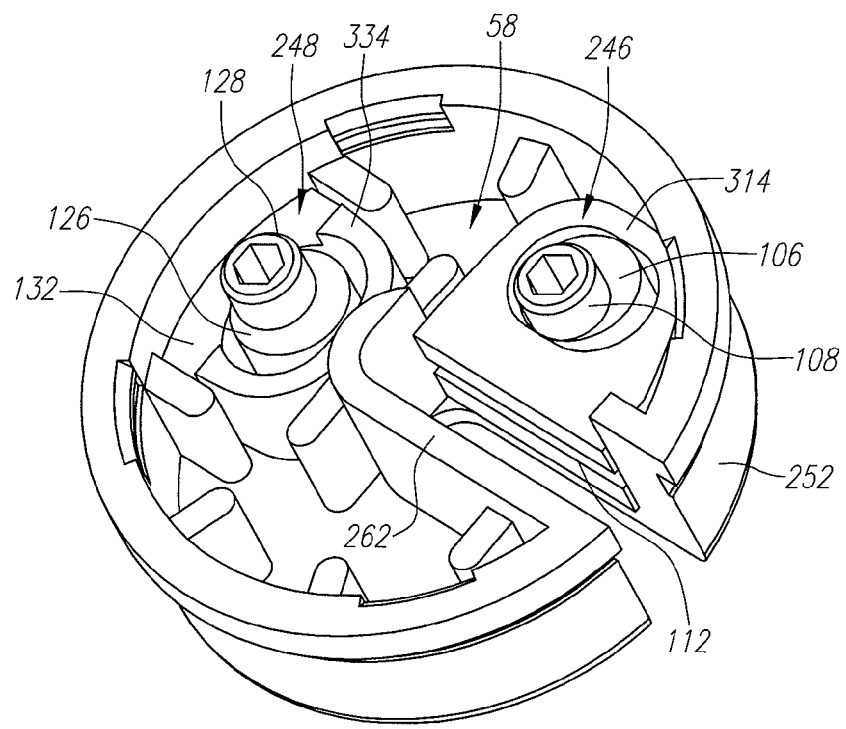
FIG. 28 is a top perspective view of the retainer of FIG. 25 with the lid removed, particularly showing the stimulation lead and plug base clamping mechanisms in their fully recessed positions.
Figure 29:
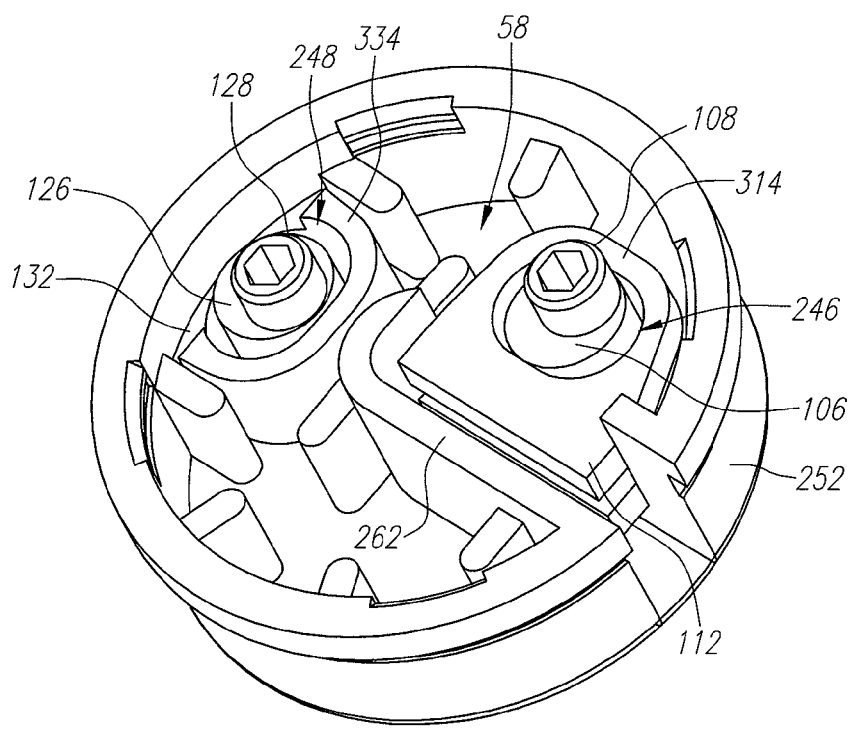
FIG. 29 is a top perspective view of the retainer of FIG. 25 with the lid removed, particularly showing the stimulation lead and plug base clamping mechanisms in their fully deployed positions.
Figure 30:
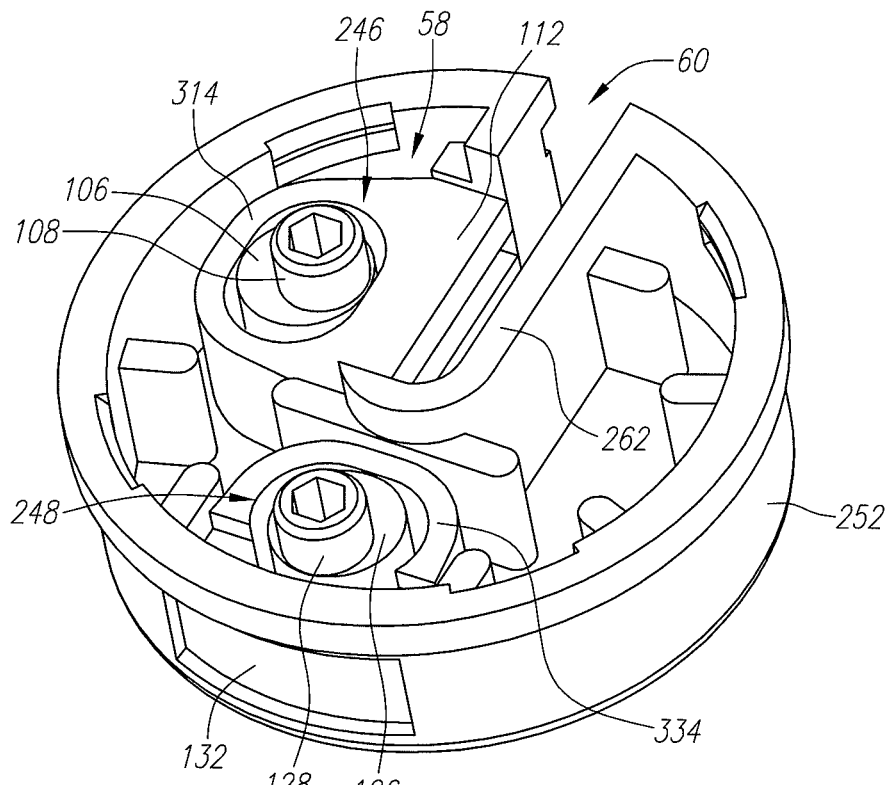
FIG. 30 is another top perspective view of the retainer of FIG. 25 with the lid removed, particularly showing the stimulation lead and plug base clamping mechanisms in their fully recessed positions.
Figure 31:
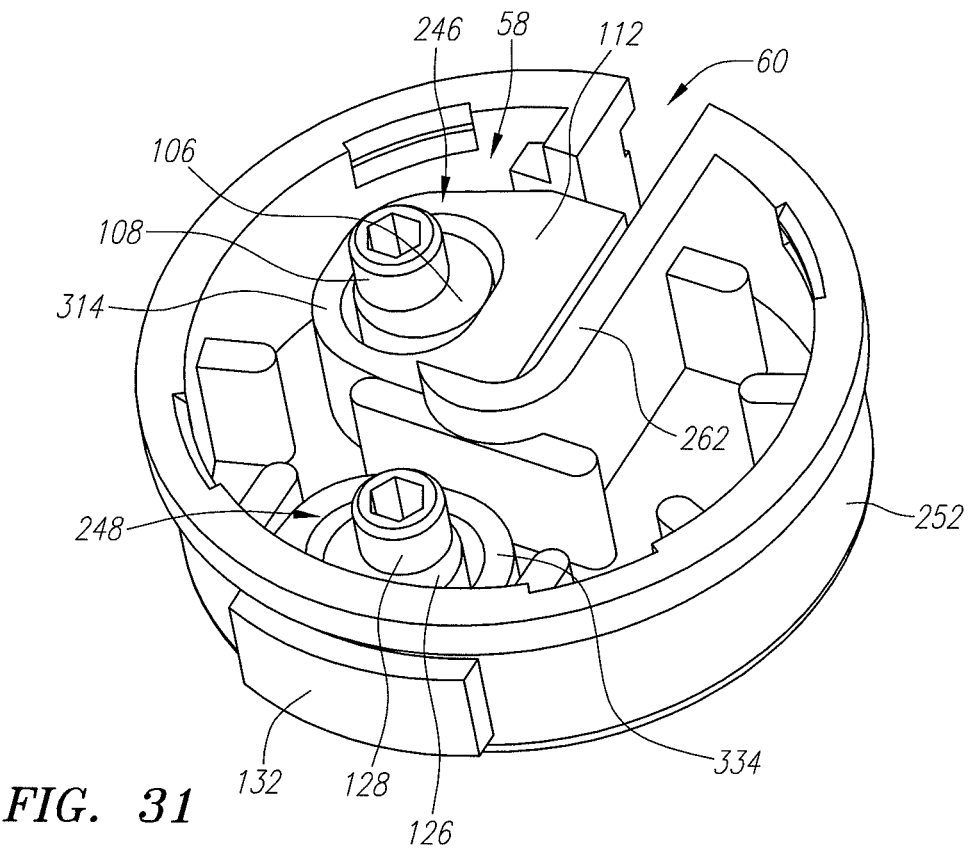
FIG. 31 is another top perspective view of the retainer of FIG. 25 with the lid removed, particularly showing the stimulation lead and plug base clamping mechanisms in their fully deployed positions.
Figure 32:
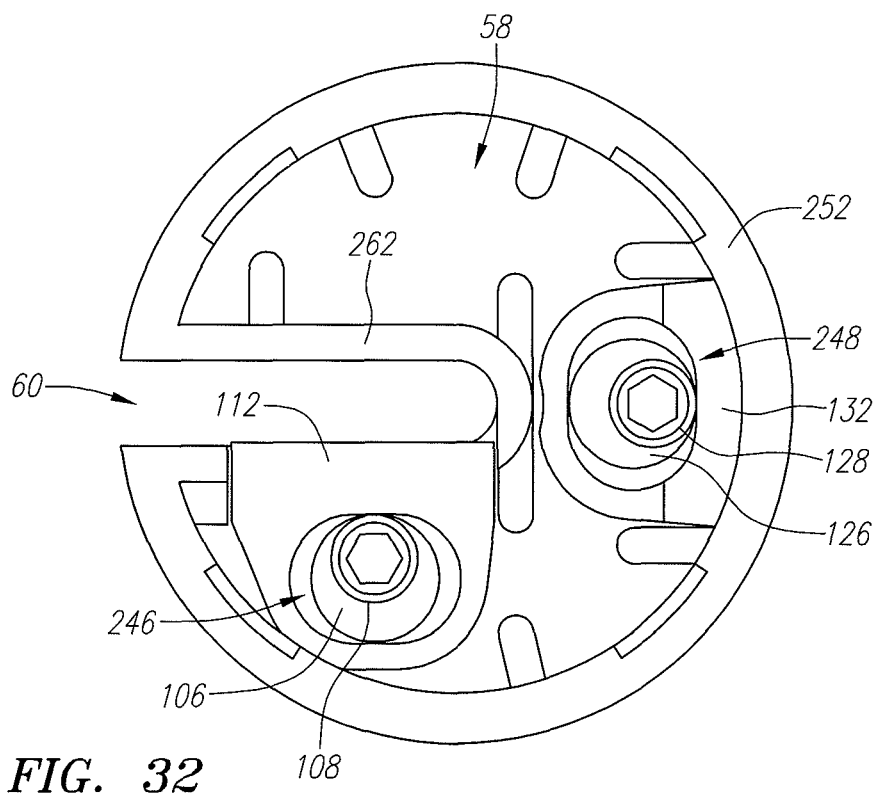
FIG. 32 is a top view of the retainer of FIG. 25 with the lid removed, particularly showing the stimulation lead and plug base clamping mechanisms in their fully recessed positions.
Figure 33:
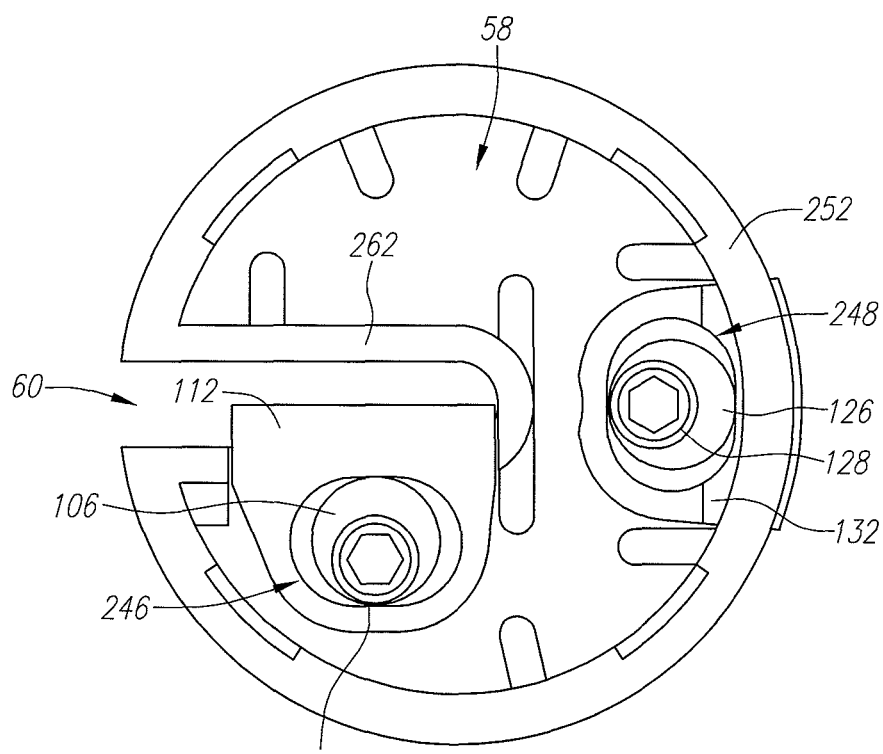
FIG. 33 is a top view of the retainer of FIG. 25 with the lid removed, particularly showing the stimulation lead and plug base clamping mechanisms in their fully deployed positions.
Figure 34:
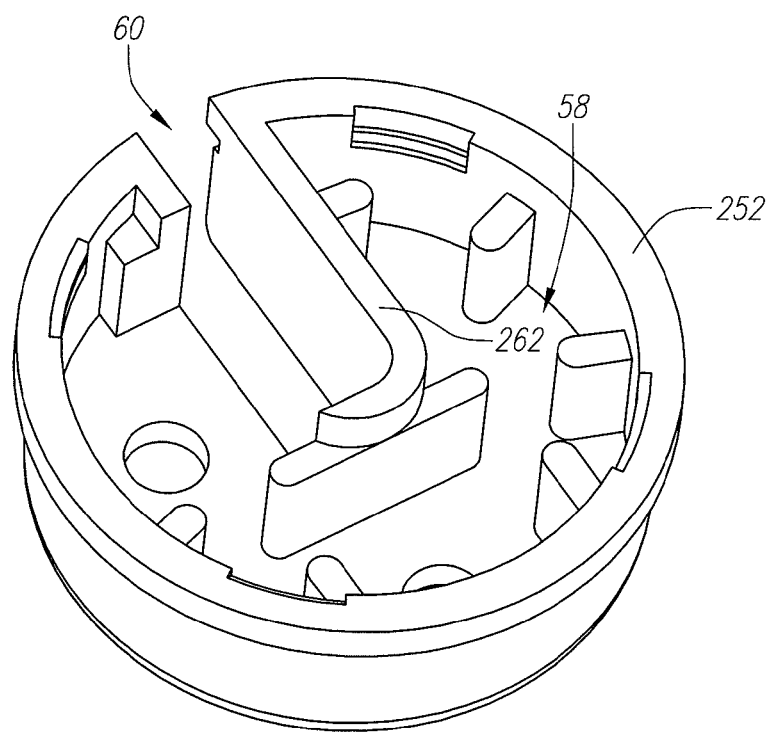
FIG. 34 is a top perspective view of a retainer support used in the retainer of FIG. 25.
Figure 35:
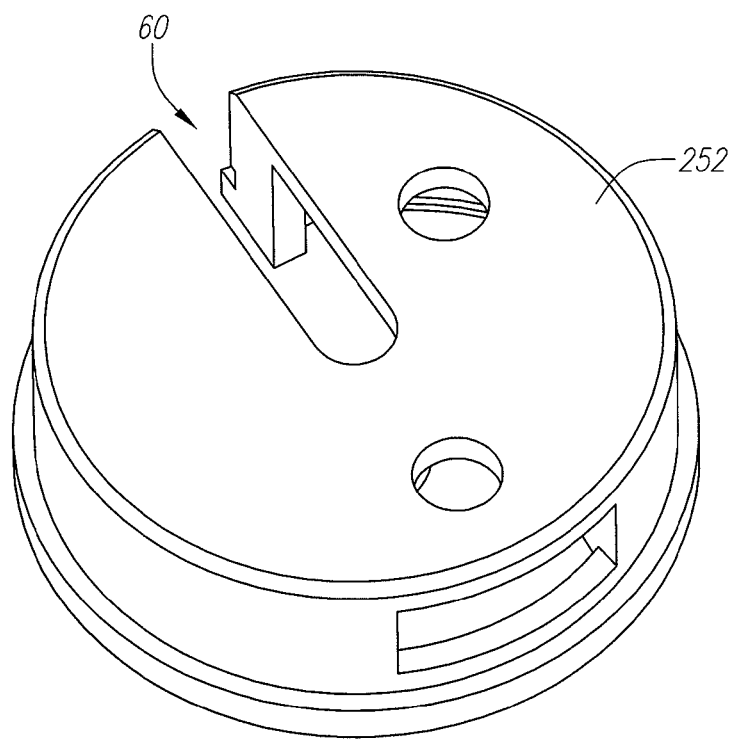
FIG. 35 is a bottom perspective view of a retainer support used in the retainer of FIG. 25.

Referring now to FIGS. 25-35, an alternative embodiment of a retainer 220 that can be mounted within the plug base 18 will be described. The retainer 220 is similar to the retainer 20, with the exception that it comprises a retainer housing 252 with an inner J-shaped sidewall 262 (instead of an inner U-shaped sidewall) that extends along one side of, and wraps around the end of, the lead slot 60, as shown in FIG. 34. Thus, the lead slot 60 is completely open to the cavity 58 within the retainer housing 252. The retainer 220 also comprises a lid 250 that is similar to the lid 50, with the exception that it comprises a slot 297 that accommodates the inner J-shaped sidewall 262 of the retainer housing 252, as shown in FIG. 25. The retainer 220 also comprises a lead clamping mechanism 246 and a base clamping mechanism 248 that are respectively similar to the lead clamping mechanism 46 and base clamping mechanism 48, with the exception that they are respectively configured for being actuated to additionally release the stimulation lead and the plug base 18.

In particular, and with specific reference to FIGS. 28-33, instead of having a pair of limiting tabs, the lead clamping mechanism 246 includes a cam follower element 314 in the shape of a collar that surrounds the cam 106. The cam follower element 314 is oblong or oval-shaped, and is oriented, such that an imaginary line drawn through its smallest dimension is perpendicular to the lead slot 60. In this manner, the cam 106 is capable of slidably engaging the opposite portions of the cam follower element 314 that are coincident with the imaginary line. Thus, rotation of the cam shaft 108 in one direction rotates the cam 106, which in turn, linearly translates the clamping flange 112 into the lead slot 60 as the cam 106 slidably engages the portion of the cam follower element 314 closest to the lead slot 60. Continued rotation of the cam shaft 108 in the same direction or rotation of the cam shaft 108 in the opposite direction, rotates the cam 106, which in turn, linearly translates the clamping flange 112 away from the lead slot 60 as the cam 106 slidably engages the portion of the cam follower element 314 furthest from the lead slot 60. Thus, the movable clamping element 104 can be displaced from a fully recessed position (FIGS. 28, 30, and 32) to a fully deployed position (FIGS. 29, 31, and 32) by rotating the cam shaft 108, and thus the cam 106, over an angle of 180 degrees from its initial position, and then displaced back to the fully recessed position by rotating the cam shaft 108, and thus the cam 106, back to its initial position.

Similarly, instead of having a pair of limiting tabs, the base clamping mechanism 248 includes a cam follower element 334 in the shape of a collar that surrounds the cam 126. The cam follower element 334 is oblong or oval-shaped, and is oriented, such that an imaginary line drawn through its smallest dimension is perpendicular to the outer sidewall opening 72. In this manner, the cam 126 is capable of slidably engaging the opposite portions of the cam follower element 334 that are coincident with the imaginary line. Thus, rotation of the cam shaft 128 in one direction rotates the cam 126, which in turn, linearly translates the clamping flange 112 through the outer sidewall opening 72 and into the annular space (not shown) formed between the retainer housing 252 and the inner flange 28 of the plug base 18 as the cam 126 slidably engages the cam follower element slidably engages the portion of the cam follower element 334 closest to the outer sidewall opening 72. Continued rotation of the cam shaft 128 in the same direction or rotation of the cam shaft 128 in the opposite direction, rotates the cam 126, which in turn, linearly translates the clamping flange 132 through the outer sidewall opening 72 away from the annular space formed between the retainer housing 252 and the inner flange 28 of the plug base 18 as the cam 106 slidably engages the portion of the cam follower element 334 furthest from the outer sidewall opening 72. Thus, the movable clamping element 124 can be displaced from a fully recessed position (FIGS. 28, 30, and 32) to a fully deployed position (FIGS. 29, 31, and 32) by rotating the cam shaft 128, and thus the cam 126, over an angle of 180 degrees from its initial position, and then displaced back to the fully recessed position by rotating the cam shaft 128, and thus the cam 126, back to its initial position.

Referring now to FIGS. 36-49, another embodiment of a burr hole plug 416 will now be described. The burr hole plug 416 differs from the previously described burr hole plug 16 in that it does not include a removable retainer. Instead, the clamping mechanisms are integrated directly into the plug base to allow the burr hole plug 416 to be removably secured within a burr hole, in addition to securing the stimulation lead.

Figure 36:
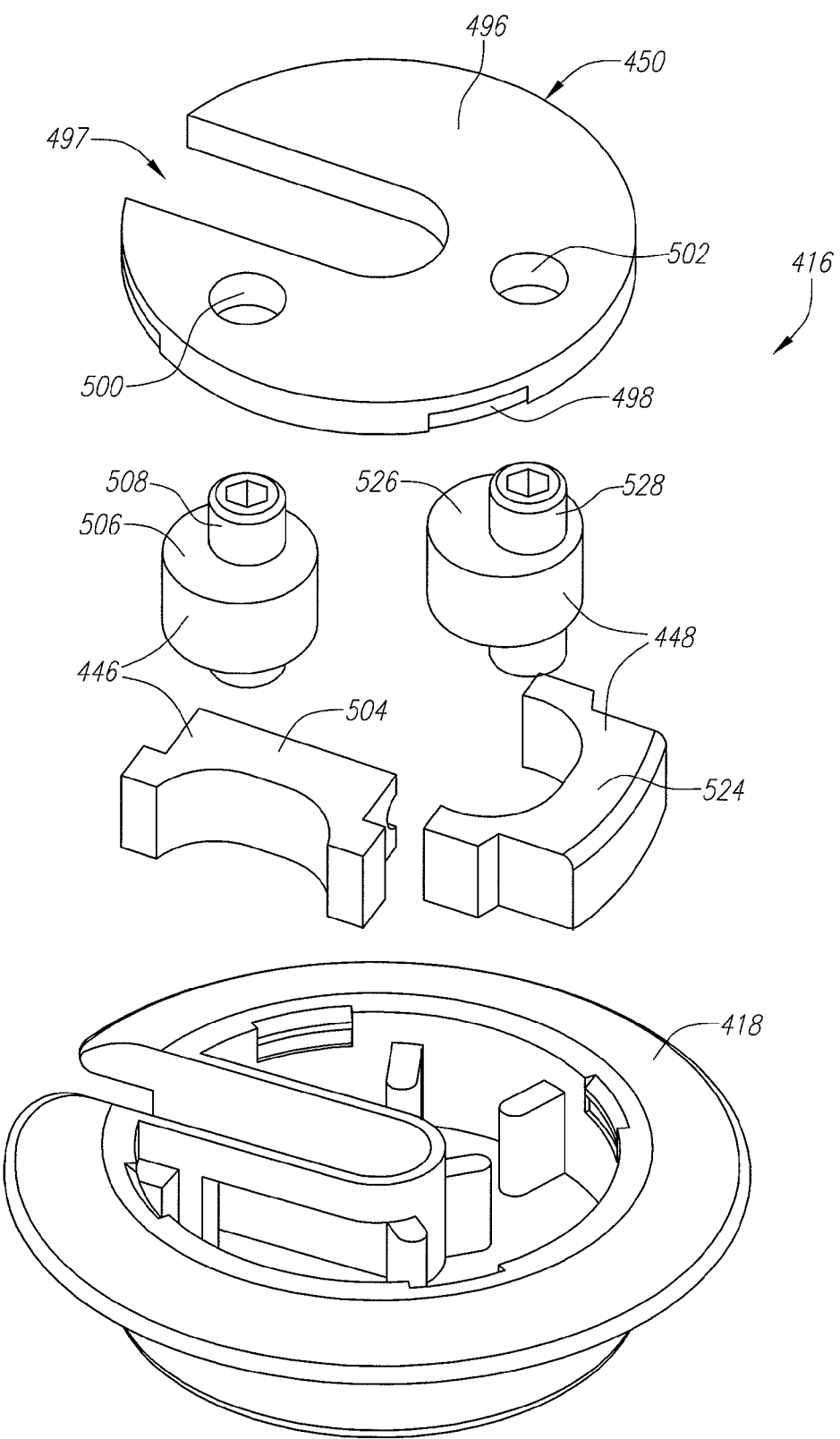
FIG. 36 is an exploded view of a burr hole plug constructed in accordance with another embodiment of the present inventions.
Figure 37:
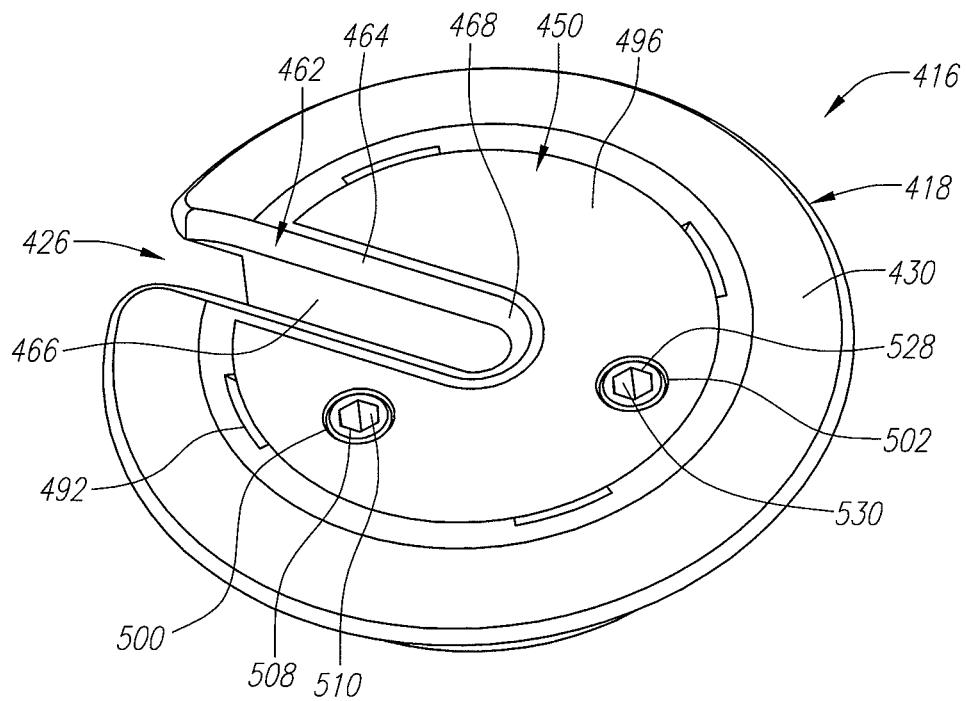
FIG. 37 is a top perspective view of the burr hole plug of FIG. 36.
Figure 38:
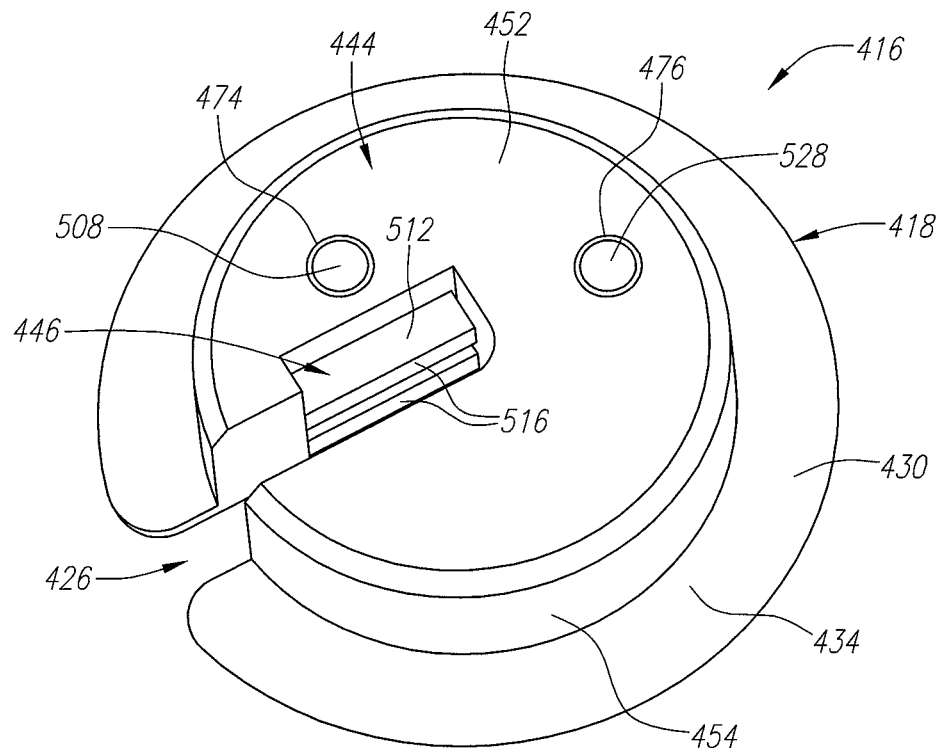
FIG. 38 is a bottom perspective view of the burr hole plug of FIG. 36, particularly showing stimulation lead and burr hole clamping mechanisms in their fully recessed positions.
Figure 39:
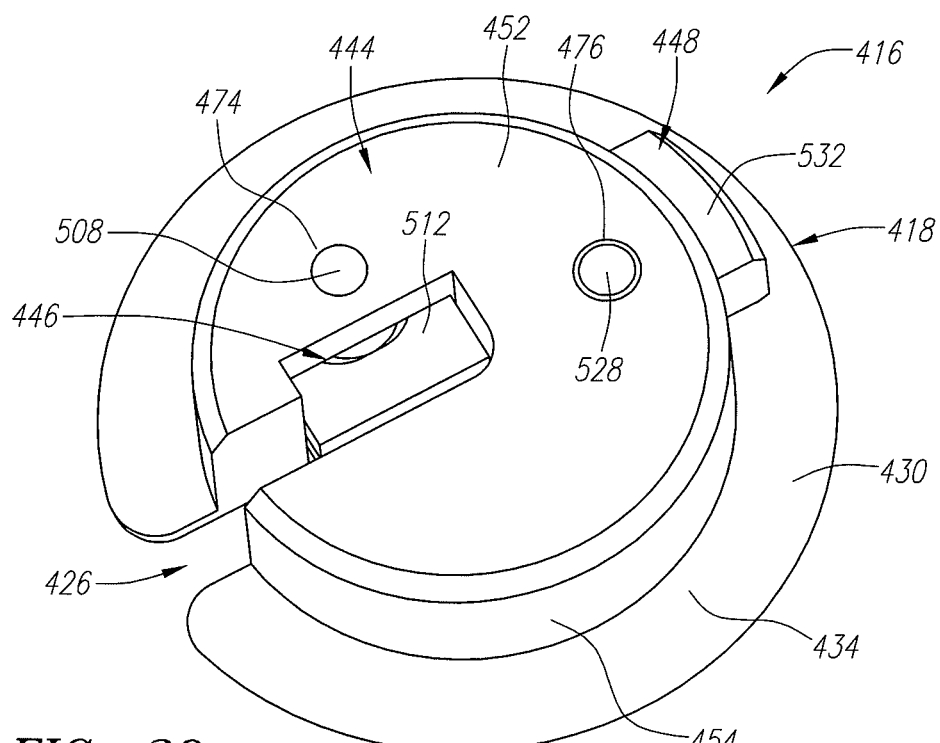
FIG. 39 is a bottom perspective view of the burr hole plug of FIG. 36, particularly showing stimulation lead and burr hole clamping mechanisms in their fully deployed positions.
Figure 40:
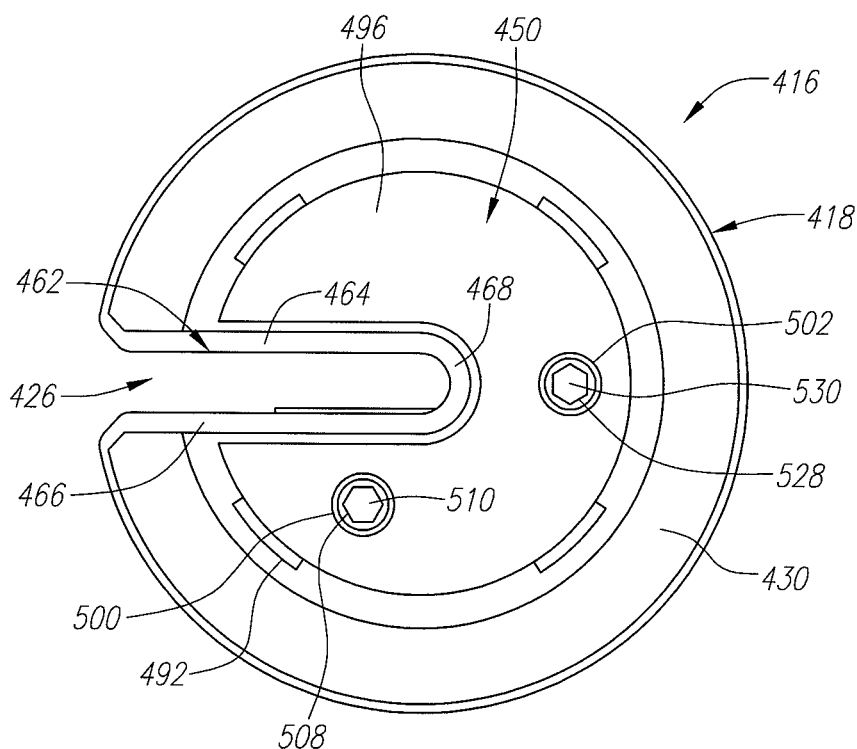
FIG. 40 is a top view of the burr hole plug of FIG. 36, particularly showing the stimulation lead clamping mechanism in its fully recessed position.
Figure 41:
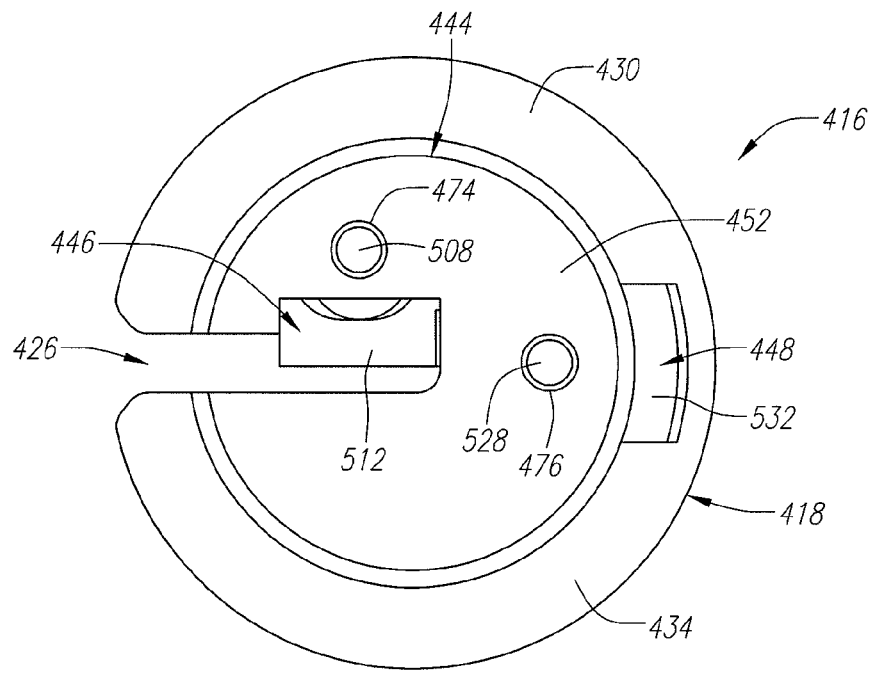
FIG. 41 is a bottom view of the burr hole plug of FIG. 36, particularly showing the stimulation lead and burr hole clamping mechanisms in their fully deployed positions.

To this end, and as clearly shown in FIG. 36, the burr hole plug 416 generally comprises a plug base (or shell) 418 configured for being fixably mounted about a burr hole, a lead clamping mechanism 446 configured for securing a stimulation lead received into the plug base 418, a burr hole clamping mechanism 448 configured for securing the plug base 418 within the burr hole, and a lid 450 configured for containing the clamping mechanisms 446, 448 within the plug base 418. As with the previous burr hole plug 16, an optional cap (not shown) can be mounted to the plug base 418 in order to seal the burr hole. Notably, the burr hole plug 416 does not comprise separate fasteners, although in alternative embodiments, they can be used as an additional means for securing the plug base 18 to the cranium. Any of the components of the burr hole plug 416 may be composed of a suitable hard biocompatible material, such as titanium, stainless steel (e.g., MP35N), alloys, or hard polymers (e.g., a high durometer silicone, polyurethane, or polyethertheterketone (PEEK)).

Figure 42:
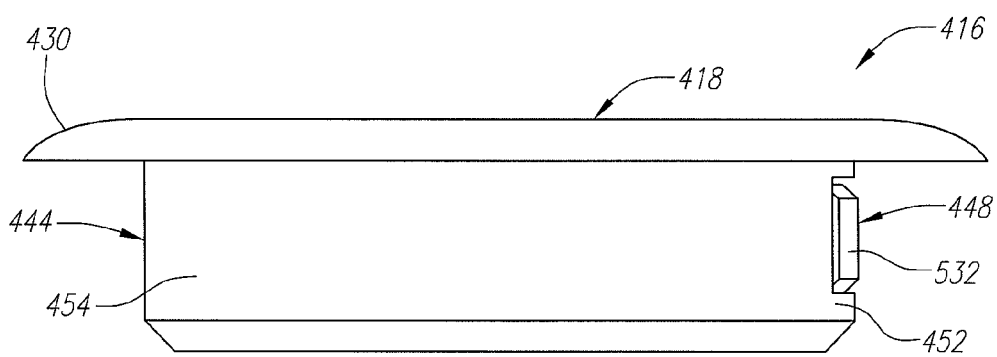
FIG. 42 is a side view of the burr hole plug of FIG. 36, particularly showing the burr hole clamping mechanism in its fully recessed position.
Figure 43:
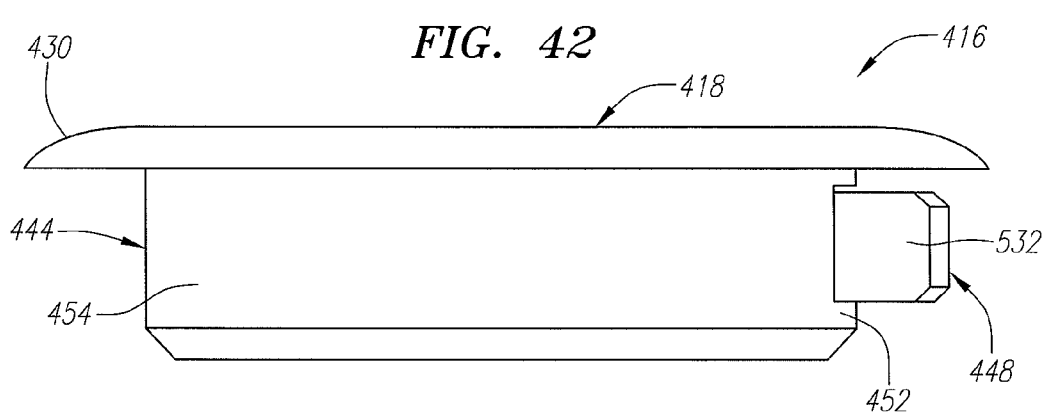
FIG. 43 is a side view of the burr hole plug of FIG. 36, particularly showing the burr hole clamping mechanism in its fully deployed position.
Figure 44:
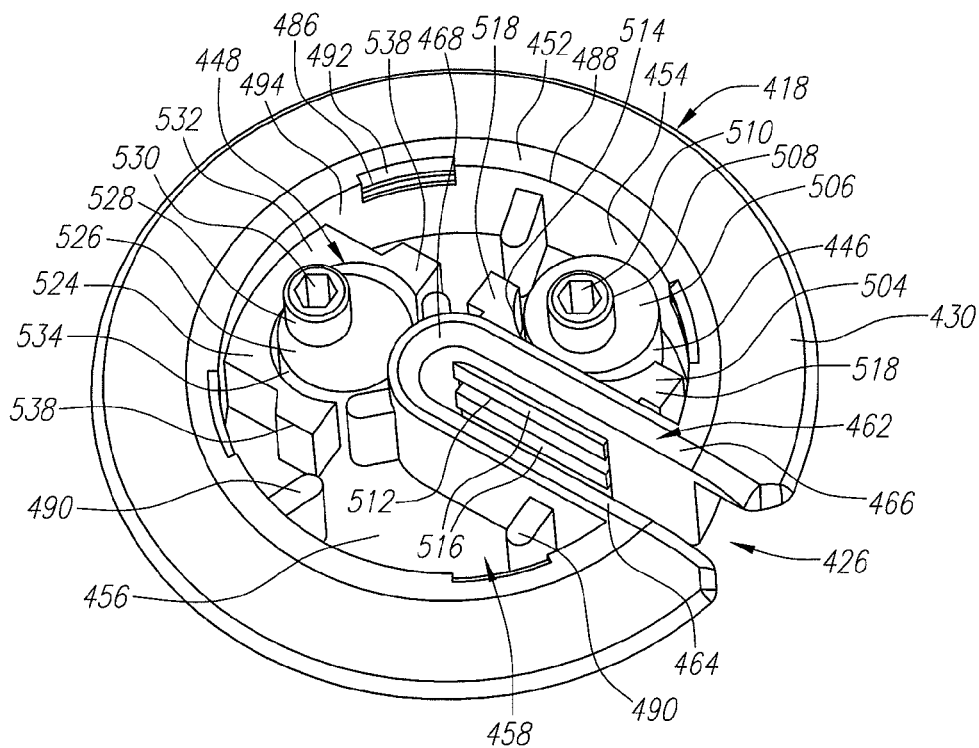
FIG. 44 is a top perspective view of the burr hole plug of FIG. 36 with the lid removed, particularly showing the stimulation lead and burr hole clamping mechanisms in their fully recessed positions.
Figure 45:
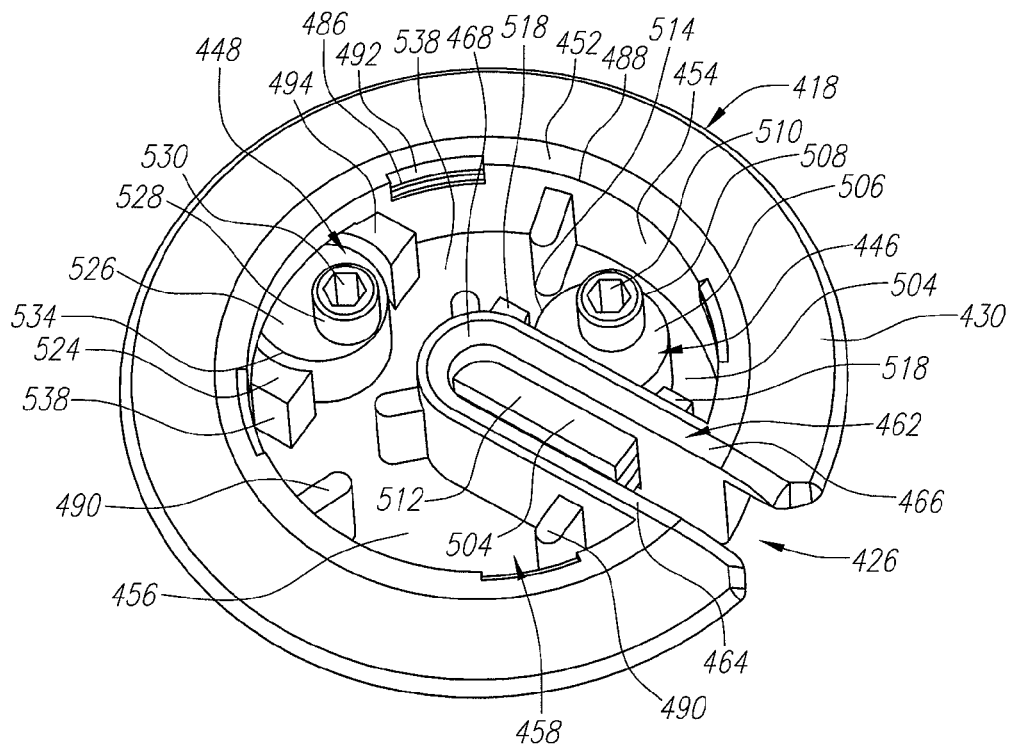
FIG. 45 is a top perspective view of the burr hole plug of FIG. 36 with the lid removed, particularly showing the stimulation lead and burr hole clamping mechanisms in their fully deployed positions.
Figure 46:
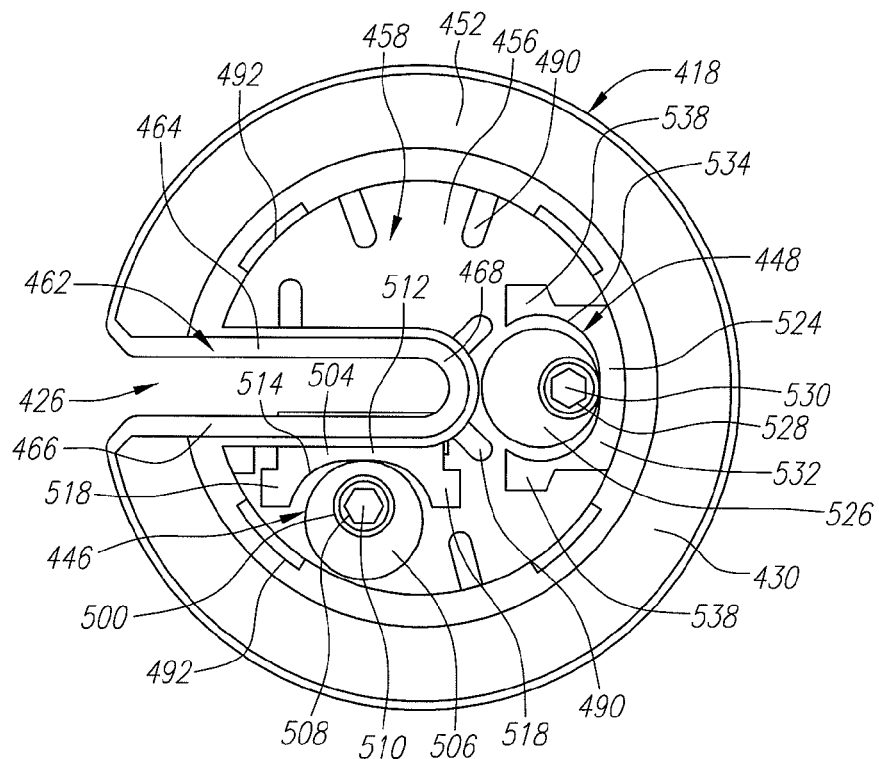
FIG. 46 is a top view of the burr hole plug of FIG. 36 with the lid removed, particularly showing the stimulation lead and burr hole clamping mechanisms in their fully recessed positions.
Figure 47:
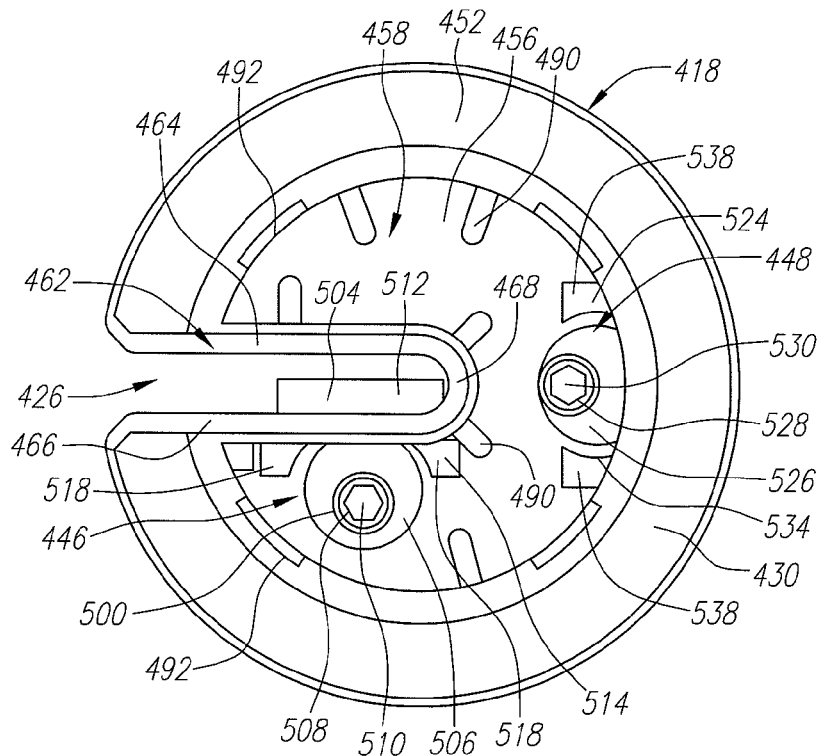
FIG. 47 is a top view of the burr hole plug of FIG. 36 with the lid removed, particularly showing the stimulation lead and burr hole clamping mechanisms in their fully deployed positions.
Figure 48:
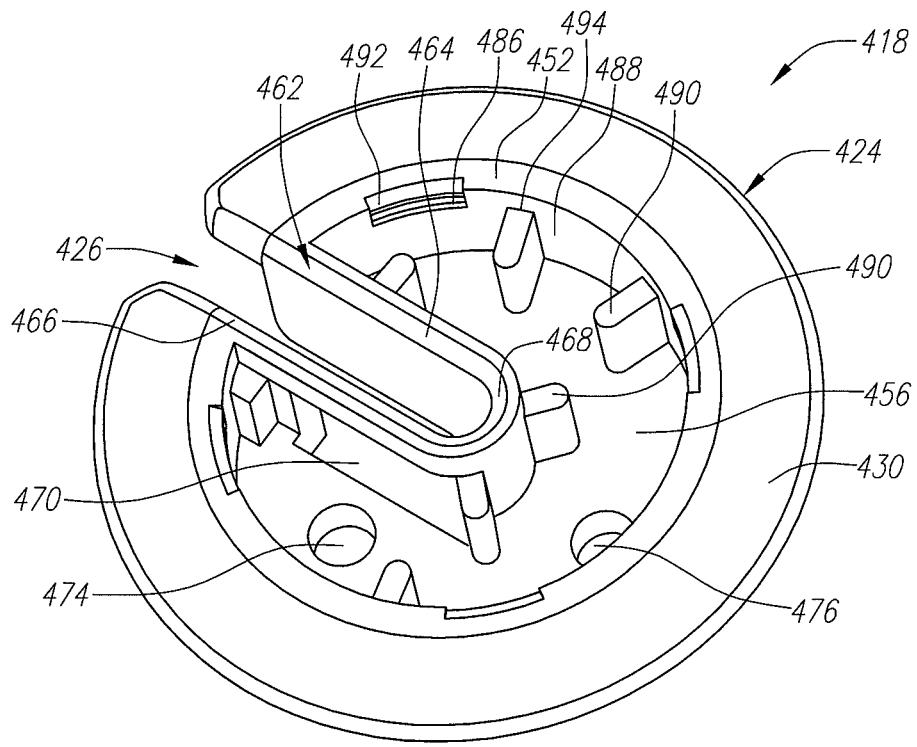
FIG. 48 is a top perspective view of a plug base used in the burr hole plug of FIG. 36.
Figure 49:
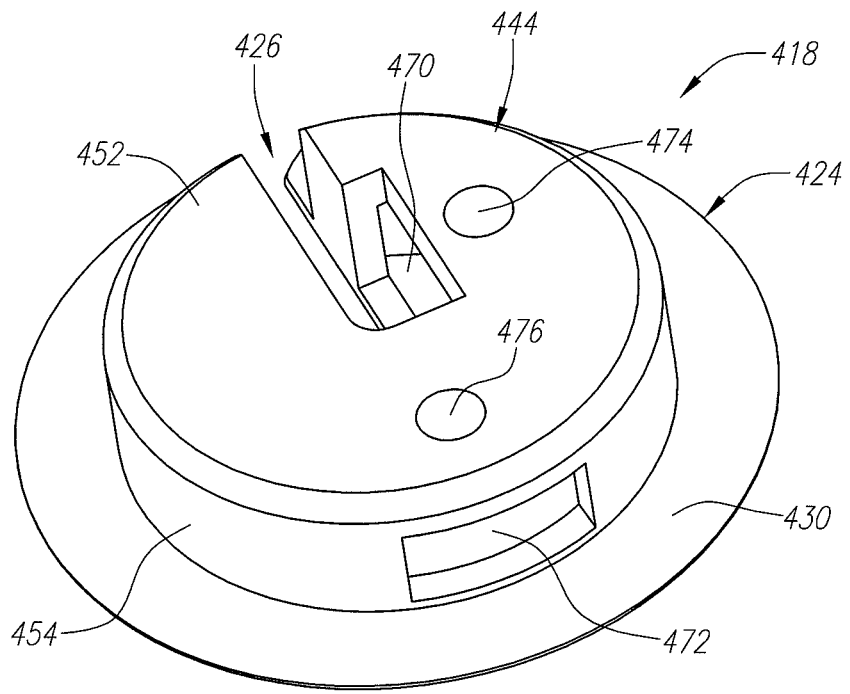
FIG. 49 is a bottom perspective view of a plug base used in the burr hole plug of FIG. 36.

As best shown in FIGS. 48 and 49, the plug base 418 includes a disk-shaped body 424 and a slot 426 formed within the plug body 424 to laterally receive the stimulation lead. This permits the plug base 418 to be mounted to the cranium around the burr hole after the stimulation lead has been inserted through the burr hole and into the brain tissue by simply sliding the stimulation lead through the slot 426 as the plug base 418 is moved into place. Like the previous plug body 24, the profile of the plug body 424 is preferably minimized as much as possible, such that the plug base 418 does not noticeably protrude from the cranium underneath the scalp of the patient. To this end, the plug base 424 comprises a retainer support 444 configured for being disposed within the cranial burr hole, and an outer circular flange 430 orthogonally extending radially outward from the top of the retainer support 444, such that the outer flange 430 is configured to reside outside of the cranial burr hole on top of the cranium when the retainer support 444 is disposed within the cranial burr hole. As a result, the height of the profile of the burr hole plug 416 above the cranial burr hole is equal to the thickness of the outer flange 430 (as best shown in FIGS. 42 and 43), thereby reducing the visibility of the burr hole plug 416 below the patient's scalp. The outer diameter of the retainer support 444 preferably matches the size of the cranial burr hole, such that an outer surface of the retainer support 444 firmly engages the cranial burr hole. In this case, the greatest dimension (in this case, its diameter) of the retainer support 444 may be in the range of 10 mm-20 mm. The bottom surface 434 of the ring-shaped body 424 may optionally be concave (not shown) in order to match the curvature of a typical cranium. As briefly discussed above, the plug base 418 need not be permanently anchored to the cranium of the patient, and thus does not include fastening holes formed within the outer flange 430.

In many respects, the retainer support 444 is similar to the retainer support 44 described above, with the exception that it somewhat larger in order to be firmly received within the burr hole. To this end, the retainer support 444 comprises a retainer housing 452 having an outer annular or cylindrical sidewall 454, a bottom floor 456, and a cavity 458 in which the clamping mechanisms 446, 448 are disposed. As illustrated, the lead slot 426 radially extends through the center of the retainer housing 452. The lead slot 426 may alternatively terminate at or short of the center of the retainer housing 452 or may be offset from the center of the retainer housing 452. The retainer housing 452 further comprises an inner U-shaped sidewall 462 that extends around the lead slot 426. The inner sidewall 462 has two straight sidewall portions 464, 466 that extend along opposite sides of the lead slot 426, and a curved sidewall portion 468 that connects the straight sidewall portions 464, 466 at the end of the lead slot 426.

The retainer support 444 further comprises a first opening 470 formed in one of the straight sidewall portions 464, 466 and a second opening 472 formed in the outer sidewall 454. As will be described in further detail below, the first and second openings 470, 472 respectively accommodate movement of the lead and base clamping mechanisms 446, 448. The retainer support 444 further comprises first and second holes 474, 476 formed through the bottom floor 456 of the retainer housing 452 to which certain elements of the lead and base clamping mechanisms 446, 448 are mounted, as will also be described in further detail below.

The retainer support 444 is configured for receiving the lid 450 in an interference arrangement, and in particular, a snap-fit arrangement. To this end, the retainer support 444 further comprises a plurality of lid locking recesses 486 formed in the inner surface 488 of the outer sidewall 454. As will be described in further detail below, the lid locking recesses 486 can receive corresponding lid locking ridges (described below) for facilitating mounting of the lid 450 to the retainer housing 452. Alternatively, the lid 450 can be secured to the retainer housing 452 using a threaded arrangement or bonding means, such as heat welding. The retainer support 444 further comprises a plurality of tab-like ledges 490 extending along the bottom floor 456 from the outer sidewall 454 and the inner sidewall 462. Each of the ledges 490 has a height that is flush with the lid locking recesses 486, such that the ledges 490 prevent the movement of the lid 450 past the lid locking recesses 486, thereby facilitating mounting of the lid 450 onto the retainer housing 452. The retainer support 444 further comprises a plurality of corresponding lid pop-out recesses 492 located at a top inner edge 494 of the outer sidewall 454 such that a tool (not shown) can be inserted into one of the lid pop-out recesses 492 to remove the previously mounted lid 450 from the retainer housing 452.

The lid 450 is similar to the lid 50 described above, with the exception that it is somewhat larger to accommodate the larger cavity 458 of the retainer housing 452. As best shown in FIG. 36, the lid 450 further comprises a disk-shaped flange 496, a slot 497 formed within the disk-shaped flange 496 that accommodates the inner sidewall 462 of the retainer housing 452, and a plurality of ridges 498 (in this case four) equally spaced around the edge of the disk-shaped flange 496 for being received within the lid locking recesses 486 formed around the inner surface 488 of the outer sidewall 454 of the retainer housing 452. The lid 450 further comprises first and second holes 500, 502 formed through the disk-shaped flange 496 for providing access to the clamping mechanisms 446, 448, as will be described in further detail below.

Referring specifically to FIGS. 44-47, the structure and operation of the lead clamping mechanism 446 is similar to that of the lead clamping mechanism 46 discussed above. In particular, the lead clamping mechanism 446 comprises a movable clamping element 504 slidably disposed on the bottom floor 456 of the retainer housing 452, a cam 506 slidably engaged with the movable clamping element 504, and a cam shaft 508 on which the cam 506 is affixed. The cam shaft 508 is rotatably mounted within the first hole 474 formed in the bottom floor 456 of the retainer housing 452, such that it can be rotated about a fixed axis to rotate the cam 506 relative to the retainer support 444. The end of the cam shaft 508 includes a tool engagement element 510 for engaging a tool (not shown) that can provide a mechanical advantage for rotation of the cam 506. The details of the tool engagement element 510 may be the same as those of the tool engagement element 110 described above. The location of the first hole 474 in the bottom floor 456 of the retainer housing 452 corresponds to the first hole 500 in the lid 450 (shown in FIG. 36), such that the end of the cam shaft 508 is seated within the first hole 500 to provide access to the tool engagement element 510.

The movable clamping element 504 comprises a clamping flange 512 configured for engaging the medical device, and a cam follower element 514 with which the cam 506 slidably engages. The cam 506 and cam shaft 508 are in an eccentric relationship, such that rotation of the cam shaft 508 about the fixed axis (i.e., the axis extending through the first hole 474) rotates the cam 506, which in turn, linearly translates the clamping flange 512 through the inner sidewall opening 440 and into the lead slot 426 as the cam 506 slidably engages the cam follower element 514. In the illustrated embodiment, the movable clamping element 504 can be displaced from a fully recessed position (FIGS. 38, 40, 44, and 46) to a fully deployed position (FIGS. 39, 41, 45, and 47) by rotating the cam shaft 508, and thus the cam 506, over an angle of 180 degrees from its initial angular position. However, other angular ranges be used to displace the movable clamping element 504 between the fully recessed position and the fully deployed position. In the illustrated embodiment, the cam 506 is circular, although in alternative embodiments, can be other shapes, including oval or oblong.

In the illustrated embodiment, the clamping flange 512 includes two horizontal and parallel ridges 516 that facilitate retention of the stimulation lead. The movable clamping element 504 may be composed of a high friction material, such as a high durometer silicone or polyurethane, to maximize lead retention. The straight sidewall portion 464 on the other side of the lead slot 426 serves as a fixed clamping element with which the movable clamping element 504 cooperates to secure the stimulation lead therebetween. To ensure that the movable clamping element 504 smoothly slides out into the lead slot 426 without rotating, the width of the clamping flange 512 is slightly less than the width of the inner sidewall opening 470, such that the sides of the clamping flange 512 slidably engage the edges of the inner sidewall opening 470. The movable clamping element 504 further comprises a pair of opposing limiting tabs 518 outwardly extending away from the cam follower element 514. These limiting tabs 518 will abut the straight sidewall portion 466 to limit movement of the clamping element 504 through the inner sidewall opening 470, thereby preventing the clamping element 504 from falling into the lead slot 426. As described above with respect to the lead clamping mechanism 46, the lead clamping mechanism 446 may include one or more spring elements, a ratchet feature or a one-way clutch feature (not shown), and an override feature, such as a push-button release (not shown).

The structure and operation of the burr hole clamping mechanism 448 is similar to that of the base clamping mechanism 48 discussed above. In particular, the burr hole clamping mechanism 448 comprises a movable clamping element 524 slidably disposed on the bottom floor 456 of the retainer housing 452, a cam 526 slidably engaged with the movable clamping element 524, and a cam shaft 528 on which the cam 526 is affixed. The cam shaft 528 is rotatably mounted within the second hole 476 formed in the bottom floor 456 of the retainer housing 452, such that it can be rotated about a fixed axis to rotate the cam 526 relative to the retainer support 444. The end of the cam shaft 528 includes a tool engagement element 530 for engaging a tool (not shown) that can provide a mechanical advantage for rotation of the cam 526. The details of the tool engagement element 530 may be the same as those of the tool engagement element 130 described above. The location of the second hole 476 in the bottom floor 456 of the retainer housing 452 corresponds to the second hole 502 in the lid 350 (shown in FIG. 36), such that the end of the cam shaft 528 is seated within the second hole 502 to provide access to the tool engagement element 530.

The movable clamping element 524 comprises a clamping flange 532 configured for engaging the burr hole (not shown), and a cam follower element 534 with which the cam 526 slidably engages. The cam 526 and cam shaft 528 are in an eccentric relationship, such that rotation of the cam shaft 528 about the fixed axis (i.e., the axis extending through the second hole 476) rotates the cam 526, which in turn, linearly translates the clamping flange 532 through the outer sidewall opening 472 and into an annular space (not shown) formed between the retainer housing 452 and the burr hole as the cam 526 slidably engages the cam follower element 534. In the illustrated embodiment, the movable clamping element 524 can be displaced from a fully recessed position (FIGS. 38, 42, 44, and 46) to a fully deployed position (FIGS. 39, 41, 43, 45, and 47) by rotating the cam shaft 528, and thus the cam 526, over an angle of 180 degrees from its initial angular position. However, other angular ranges be used to displace the movable clamping element 524 between the fully recessed position and the fully deployed position. In the illustrated embodiment, the cam 526 is circular, although in alternative embodiments, can be other shapes, including oval or oblong.

To ensure that the movable clamping element 524 smoothly slides out into the annular space between the outer sidewall 454 of the retainer housing 452 and the burr hole, the width of the clamping flange 532 is slightly less than the width of the outer sidewall opening 472, such that the sides of the clamping flange 532 slidably engage the edges of the outer sidewall opening 472. The movable clamping element 504 further comprises a pair of opposing limiting tabs 538 outwardly extending away from the cam follower element 534. These limiting tabs 538 will abut the inner surface of the outer sidewall 454 to limit movement of the clamping element 524 through the outer sidewall opening 472, thereby preventing the clamping element 524 from falling into the annular space. As described above with respect to the retainer clamping mechanism 48, the burr hole clamping mechanism 448 may include one or more spring elements, a ratchet feature or a one-way clutch feature (not shown), and an override feature, such as a push-button release (not shown).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A cranial burr hole plug, comprising:
   a plug base configured for being mounted around a cranial burr hole, the plug base including an aperture through which an elongated medical device exiting the burr hole may pass; and
   a retainer configured for being mounted within the aperture of the plug base, the retainer including a retainer support, a slot formed in the retainer support for receiving the medical device, and a clamping mechanism having a movable clamping element and a cam configured for being rotated relative to the retainer support to linearly translate the movable clamping element into the slot, thereby securing the medical device.

2. The burr hole plug of claim 1, wherein the retainer is configured for being removably mounted within the aperture of the plug base.

3. The burr hole plug of claim 1, wherein the plug base includes at least one inner annular ledge configured for supporting the retainer when mounted within the aperture of the plug base.

4. The burr hole plug of claim 1, wherein the retainer support includes a housing that contains the clamping mechanism.

5. The burr hole plug of claim 4, wherein the retainer further comprises a lid configured for being mounted to the housing to enclose the clamping mechanism.

6. The burr hole plug of claim 4, wherein the housing has a sidewall and an opening within the sidewall through which the movable clamping element is configured for linearly translating into the slot.

7. The burr hole plug of claim 1, wherein the clamping mechanism further comprises a shaft rotatably mounted to the retainer support, the cam being affixed to the shaft.

8. The burr hole plug of claim 7, wherein the shaft and cam are eccentrically disposed relative to each other.

9. The burr hole plug of claim 7, wherein the shaft is configured for receiving a tool for rotating the shaft.

10. The burr hole plug of claim 1, wherein the cam is configured for being rotated relative to the retainer support to linearly translate the movable clamping element out of the slot, thereby releasing the medical device.

11. The burr hole plug of claim 1, wherein the movable clamping element comprises a clamping flange configured for engaging the medical device and a cam follower element with which the cam slidably engages.

12. The burr hole plug of claim 11, wherein the cam follower element is a collar circumferentially surrounding the cam.

13. The burr hole plug of claim 1, wherein the slot is an open slot configured for laterally receiving the medical device.

14. The burr hole plug of claim 1, wherein the retainer support has a fixed clamping element on one side of the slot opposite the movable clamping element, and the movable clamping element is configured for clamping the medical lead against the fixed clamping element.

15. The burr hole plug of claim 1, wherein the retainer comprises another clamping mechanism having another movable clamping element and another cam configured for being rotated relative to the retainer support to linearly translate the other movable clamping element, thereby laterally securing the retainer within the plug base.

16. The burr hole plug of claim 1, wherein the retainer comprises another clamping mechanism having another movable clamping element and another cam configured for being rotated relative to the retainer support to linearly translate the other movable clamping element, thereby securing the plug base within the cranial burr hole.

17. The burr hole plug of claim 1, wherein the plug base comprises an inner annular flange configured for being disposed inside the cranial burr hole and an outer annular flange configured for being disposed outside of the cranial burr hole.

* * * * *